US008741635B2

(12) United States Patent
Lindeman et al.

(10) Patent No.: US 8,741,635 B2
(45) Date of Patent: Jun. 3, 2014

(54) METHOD OF CELL ISOLATION

(75) Inventors: Geoffrey John Lindeman, Kew (AU);
Mark Shackleton, Ann Arbor, MI (US);
Francois Vaillant, Geelong West (AU);
Jane Ellen Visvader, Kew (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 1458 days.

(21) Appl. No.: 11/596,397

(22) PCT Filed: May 12, 2005

(86) PCT No.: PCT/AU2005/000685
§ 371 (c)(1),
(2), (4) Date: Feb. 12, 2007

(87) PCT Pub. No.: WO2005/108981
PCT Pub. Date: Nov. 17, 2005

(65) Prior Publication Data
US 2008/0038230 A1    Feb. 14, 2008

(30) Foreign Application Priority Data

May 12, 2004    (AU) ................................ 2004902525

(51) Int. Cl.
*C12N 5/00*    (2006.01)
(52) U.S. Cl.
USPC ........................ 435/325; 435/378; 424/93.7
(58) Field of Classification Search
None
See application file for complete search history.

(56) References Cited

U.S. PATENT DOCUMENTS

2003/0082155 A1 *  5/2003  Habener et al. ............ 424/93.21
2003/0186936 A1 * 10/2003  Chaudhuri et al. ............. 514/54

OTHER PUBLICATIONS

Alvi AJ et al. 2003. Functional and molecular characterization of mammary side population cells. Breast Cancer Res 5: R1-R8.*
Stingl J et al. 2005. Purification of the adult pluripotent self-renewing mouse mammary stem cell using an in vivo assay. Proc Amer Assoc Cancer Res 2005;46: 5247. 1 page.*
Al-Hajj, A. et al. 2003 "Prospective identification of tumorigenic breast cancer cells" *Proc Natl Acad Sci U.S.A.* 100:3983-3988.
Stingl, J. et al. 2003 "Quantitation and phenotypic characterization of mouse mammary stem cells" *Proceedings of the American Association for Cancer Research* 44 $2^{nd}$ ed., p. 856, abstract #R4317.
Welm, B. et al. 2002 "Sca-$1^{pos}$ Cells in the Mouse Mammary Gland Represent an Enriched Progenitor Cell Population" *Developmental Biology* 245: 42-56.

* cited by examiner

*Primary Examiner* — Lora E Barnhart Driscoll
(74) *Attorney, Agent, or Firm* — Knobbe, Martens, Olson & Bear, LLP

(57) ABSTRACT

The present invention relates generally to a method for the generation of a substantially homogenous population of undifferentiated cells. More particularly, the present invention relates to a method for isolating a substantially homogenous population of stem cells, and in particular, mammary stem cells (MaSCs). The MaSCs of the present invention are isolated on the basis of differential levels of proteins present on their cell surface. The MaSCs of the present invention are particularly useful as targets for identifying agents which modulate MaSC survival, self-renewal, proliferation and/or differentiation in both normal and diseased tissue such as, but not limited to, tumor tissue, and, also as source of tissue for the regeneration, replacement and/or augmentation of tissue damaged and/or lost after disease or injury.

11 Claims, 17 Drawing Sheets

Sample preparation - 'same day' method (A) Harvest mammary tissue
  • 8 week old females
(B) Mechanical dissociation
(C) Enzymatic digestion
  • collagenase
  • hyaluronidase
  • trypsin
  • dispase
(D) RBC lysis
(E) Staining with antibodies

Limiting dilution analysis of the frequency of repopulating cells in the mouse mammary gland

| No. CD45$^{lo}$ cells transplanted | No. of transplants | No. of outgrowths | % |
|---|---|---|---|
| 2,500 | 6 | 3 | 50 |
| 5,000 | 8 | 6 | 75 |
| 10,000 | 9 | 9 | 100 |
| 20,000 | 9 | 9 | 100 |
| 40,000 | 2 | 2 | 100 |

Repopulating cell frequency of the PI$^{lo}$CD45$^{lo}$TER$^{lo}$ cells is 1/3000 (95%CI 1/1800 - 1/5000)

FIGURE 4

Flow cytometric analysis of surface markers on gated CD45$^{lo}$ population

Repopulation of mammary fat pads with FACS-sorted cells

100 CD24$^+$CD29$^+$ cells

8505 CD24$^-$CD29$^-$ cells

Sca-1+ cells do not have an enriched mammary repopulation capacity

CD45lo/TER119lo/CD31lo population

| No. cells transplanted | No. of transplants | No. of outgrowths |
|---|---|---|
| 2410 Sca-1- | 5 | 2 |
| 1894 Sca-1- | 7 | 2 |
| 2257 Sca-1+ | 5 | 0 |
| 2110 Sca-1+ | 6 | 0 |

METHOD OF CELL ISOLATION

RELATED APPLICATIONS

This application is a U.S. national Phase of International Application No. PCT/AU2005/000685, filed May 12, 2005.

BACKGROUND OF THE INVENTION

1. Field of the Invention

The present invention relates generally to a method for the generation of a substantially homogenous population of undifferentiated cells. More particularly, the present invention relates to a method for isolating a substantially homogenous population of stem cells, and in particular, mammary stem cells (MaSCs). The MaSCs of the present invention are isolated on the basis of differential levels of proteins present on their cell surface. The MaSCs of the present invention are particularly useful as targets for identifying agents which modulate MaSC survival, self-renewal, proliferation and/or differentiation in both normal and diseased tissue such as, but not limited to, tumor tissue, and, also as source of tissue for the regeneration, replacement and/or augmentation of tissue damaged and/or lost after disease or injury.

2. Description of the Prior Art

Reference to any prior art in this specification is not, and should not be taken as, an acknowledgment or any form of suggestion that this prior art forms part of the common general knowledge in any country.

Bibliographic details of references provided in this document are listed at the end of the specification.

Breast cancer is the most common malignancy to affect women, accounting for approximately one quarter of all female cancers. Despite a significant improvement in the management of breast cancer over the last few years, about 25% of women diagnosed will die from the disease, revealing that those tumor cells have intrinsic properties that are refractory to current treatment strategies. The heterogeneous nature of breast cancer suggests the involvement of multiple genetic factors and cell types but these are poorly understood.

A prerequisite to understanding breast oncogenesis is the study of the regulation of normal breast epithelial development. The mammary gland is composed of a branching network of ducts and lobuloaveolar structures, the latter arising through pregnancy. There are two primary epithelial cell lineages, myoepithelial and luminal (comprising ductal and alveolar subtypes), which are presumed to arise from a common progenitor cell referred to herein as a mammary stem cell or MaSC (for review see Smalley and Ashworth, *Nat Rev Cancer* 3:832-844, 2003). The concept of an organ-specific stem cell is well established for haematopoiesis, as well as other organ systems (e.g. Rietze et al., *Nature* 214:736-739, 2001; Li et al., *Nat Med* 9:1293-1299, 2003; Morris et al., *Nat Biotech* 22:411-417, 2004; Tumbar et al., *Science* 303:359-363, 2004). It has been hypothesized that stem and progenitor cells (also known as transit amplifying cells) are critical cellular targets during tumorigenesis, and that deregulated expression of genes normally expressed in mammary stem and progenitor cells contribute to the pathogenesis of breast cancer (Reya et al., *Nature* 414:105-111, 2001). The existence of a breast cancer "stem cell" may, in fact, be one explanation for resistance to existing anti-cancer drugs and eventual emergence of disease that is refractory to therapy (Al-Hajj et al., *PNAS* 100:3983-3988, 2004).

The mammary gland normally develops postnatally (at puberty), through a process of ductal elongation and branching that extends from the nipple region to penetrate the stromal tissue of the mammary gland ("the mammary fat pad" or MFP). This process is primarily driven by oestrogen and progesterone, and also requires prolactin. In the adult gland, the mammary gland is therefore comprised of the stomal elements and branching ducts. The ducts are comprised of luminal epithelial cells and surrounding myoepithelial cells, which are believed to arise from a common precursor cell. These are surrounded by a basement membrane. During pregnancy further development and functional maturation of the mammary gland occurs through additional ductal outgrowth and branching and the outgrowth of lobuloalveolar structures, which are the milk-secreting units in the fully differentiated gland. Lobuloalveolar units are comprised of alveolar epithelial and myoepithelial cells, and are also surrounded by a basement membrane. Following the cessation of lactation, the mammary gland undergoes a process of coordinated involution, whereby the lobuloalveolar units and some ducts regress through a process of programmed cell death and remodelling. This entire process undergoes repeated cycles with each pregnancy. Stem cells and progenitor cells are necessary for adult mammary gland development and the sequential rounds of epithelial cell development with each pregnancy cycle. It has been proposed that a resting stem cell undergoes coordinated lineage specification and commitment to pre-luminal or pre-myoepithelial progenitor cells, which in turn differentiate into functional ductal and alveolar luminal cells and myoepithelial cells, respectively (FIG. 1).

The existence of MaSCs has been confirmed through serial transplantation studies using epithelial mammary explants in mice (Daniel et al., *PNAS* 61:53-60, 1968). This technique involves transfer of small donor mammary explants into the de-epithelialized MFPs of pre-pubertal female recipient mice. A small fragment of epithelial tissue from a donor mouse transplanted into the cleared fat pad of a pre-pubertal mouse will reconstitute an entire mammary gland under the stimulus of pubertal and pregnancy hormones. Transplantation of epithelial cell suspensions in sufficient numbers will also reconstitute a mammary gland. The identification of MaSCs (or committed progenitors) requires the transfer of purified populations of cells to identify which population has the greatest capacity to form mammary epithelium.

In previous studies, haematopoietic stem cells have been shown to lack lineage markers such as Ter119 (erythroid), CD3 and B220 (T and B lymphoid cells), Mac-1 (myeloid) and to express high levels of c-kit and Sca-1. Haematopoietic stem cells have also been shown to exclude the vital dye Hoechst$_{33342}$ (Ho) with great efficiency, resulting in a side population (SP) in flow cytometric studies (Goodall et al., *J Exp Med* 183:1797-1806, 1996). Data using mammary epithelial cells that were propagated in vitro for several days and then purified by fluorescence-activated cell sorting (FACS) have found that Sca-1$^+$ cells exhibit enhanced Ho dye exclusion and an enriched mammary repopulating capacity, suggesting that mammary stem cells reside within this population (Welm et al., *Dev Biol* 245:42-56, 2002). In addition, a SP has been identified in and purified from more freshly isolated mammary epithelial cell preparations, and found to be able to produce mammary epithelial structures on transplantation into MFPs (Alvi et al., *Breast Cancer Res* 5:R1-R8, 2003). However, in these studies MFP repopulation required large numbers (several thousand) of cells, and the comparative repopulating capacity of purified cell populations was not evaluated at limiting dilution. Furthermore, the purified cell populations in these studies were obtained from a source of cells that had been maintained in culture. These conditions are likely to modify cell surface marker phenotype and as such, the characteristics of the purified cells in these studies are unlikely to reflect those which exist in vivo.

There is a need, therefore, for a method of isolating a substantially homogenous population of MaSCs from a source of freshly isolated tissue.

SUMMARY OF THE INVENTION

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

Abbreviations used herein are defined in Table 1.

The present invention is predicated in part by the identification that undifferentiated cells, particularly stem cells, and even more particularly mammary stem cells (MaSCs), can be isolated from a tissue source based upon differential levels of proteins present on the cell surface. In particular, discrete populations of MaSCs are isolated on the basis of cell surface markers one subpopulation (Lin$^-$CD29$^{hi}$CD24$^+$) is highly enriched for MaSCs as assayed by in vivo transplantation. By way of demonstration, a single cell, marked with a lacZ transgene, is capable of reconstituting a complete mammary gland in vivo. The transplanted cell contributed to both the luminal and myoepithelial linages and generated functional lobuloalveolar units during pregnancy. The self-renewing capacity of these cells was demonstrated by serial transplantation of clonal epithelial outgrowths. In support of a potential role for MaSCs in breast cancer, the stem cell-enriched subpopulation was markedly expanded in premalignant mammary tissue from MMTV-Wnt-1 mice. The single cells within the Lin$^-$CD29$^{hi}$CD24$^+$) population are multipotent and self-renewing, and hence define the MaSC.

The present invention provides, therefore, a method for isolating a substantially homogenous population of MaSCs cells from a biological sample said method comprising subjecting said biological sample to a tissue-disruption means to provide a heterogenous population of cells comprising the MaSCs to be isolated and subjecting said heterogenous population of cells to a cell surface marker discrimination means to isolate a substantially homogenous population of MaSCs.

The terms "tissue-disruption" and "tissue-dissociation" may be used interchangeably to refer to breaking a tissue apart to release individual cells.

The present invention advantageously provides a method for isolating MaSCs without the need to first maintain the tissue from which the MaSCs are derived in culture. As a result, the MaSCs isolated in accordance with the method of the present invention retain characteristics of MaSCs ii) vivo which may otherwise be modified or lost if the MaSCs underwent a period of culture prior to isolation.

The isolation of the MaSCs provided by the present invention may be performed using any cell-selection means which facilitates cell selection according to levels of cell surface proteins. Preferably, the cell-selection means comprises contacting the MaSCs to be selected, either sequentially or simultaneously, with molecules capable of interacting with cell surface proteins which are conjugated to a reporter compound which allows cell selection and identification. Most preferably, the molecules are conjugated to a fluorescent reporter compound, thereby facilitating cell-selection according to fluorescence intensity using fluorescence activated cell sorting (FACS).

Preferably, the isolated MaSCs of the present invention produce low levels of the cell surface proteins CD45, Lin and CD31 and high levels of the cell surface proteins CD24 and CD29 and hence the MaSCs of the present invention are referred to as CD45$^{lo}$Lin$^{lo}$CD31$^{lo}$CD24$^{hi}$CD29$^{hi}$ MaSCs.

Accordingly, the present invention contemplates a method for isolating a substantially homogenous population of CD45$^{lo}$Lin$^{lo}$CD31$^{lo}$CD24$^{hi}$CD29$^{hi}$ MaSCs from a biological sample said method comprising subjecting said biological sample to a tissue-disruption means to provide a heterogenous population of cells comprising the CD45$^{lo}$Lin$^{lo}$CD31$^{lo}$CD24$^{hi}$CD29$^{hi}$ MaSCs to be isolated and subjecting said heterogenous population of cells to a cell surface marker discrimination means to isolate a substantially homogenous population of CD45$^{lo}$Lin$^{lo}$CD31$^{lo}$CD24$^{hi}$CD29$^{hi}$ MaSCs.

The ability to isolate MaSCs according to the method of the present invention provides methods and compositions for use in tissue replacement and/or augmentation therapy, particularly mammary tissue replacement and/or augmentation therapy. In particular, the MaSCs isolated in accordance with the method of the present invention facilitate autologous cell transplant therapies and reduce, therefore, the need for allogenic tissue transplantation and the concomitant use of immunosuppressive agents.

Furthermore, the ability to isolate MaSCs according to the method of the present invention also enables the identification agents which modulate MaSC survival, self-renewal, proliferation and/or differentiation in both normal and diseased tissue in vitro and/or in vivo. In particular, the identification of agents which regulate the in vivo activity of MaSCs provides a method to induce or otherwise facilitate the regeneration and/or augmentation of tissue, particularly mammary tissue, in situ, that is, without the need for tissue transplantation.

Accordingly, the present invention contemplates the use of agents which modulate the in vitro and/or in vivo activity of MaSCs in the manufacture of a medicament for the treatment of a range of diseases, conditions and/or injuries which necessitate tissue, particularly mammary tissue, regeneration, replacement and/or augmentation.

TABLE 1

| ABBREVIATION | DESCRIPTION |
| --- | --- |
| BCIP | 5-bromo-4-chloro-3-indoyl phosphate |
| CD24$^{hi}$ | High levels of CD24 |
| CD29$^{hi}$ | High levels of CD29 |
| CD31$^{lo}$ | Low or absent levels of CD31 |
| CD45$^{lo}$ | Low or absent levels of CD45 |
| $CO_2$ | Carbon dioxide |
| DAB | 3,3',4,4''-diamnobenzidine |
| DNA | Deoxyribonucleic acid |
| DTPA | Diethylenetriaminepentaacetic acid |
| EDTA | Ethylenediaminetetraacetic acid |
| EGF | Epidermal growth factor |
| EGTA | Ethyleneglycoltetraacetic acid |
| ELISA | Enzyme linked immunosorbent assay |
| FACS | Fluorescent activated cell sorting |
| FCS | Foetal calf serum |
| FITC | Fluorescein isothiocyanate |
| GFP | Green fluorescent protein |
| HAC | Human artificial chromosome |
| Lin$^{lo}$ | Low or absent levels of Lin (same as TER119) |
| MaSC | Mammary epithelial stem cell |
| MP | Main population |
| mRNA | Messenger RNA |
| $O_2$ | Oxygen |
| PCR | Polymerase chain reaction |
| PE | Phycoerythrin |
| PI | Propidium iodide |
| PNA | Peanut agglutinin |

TABLE 1-continued

ABBREVIATIONS

| ABBREVIATION | DESCRIPTION |
| --- | --- |
| PNA | Peanut agglutinin |
| RITC | Rhodamine isothiocyanate |
| RNA | Ribonucleic acid |
| RNAi | RNA interference |
| RT-PCR | Reverse transcriptase PCR |
| siRNA | small interfering RNA |
| SP | Side population |
| TER119$^{lo}$ | Low or absent levels of TER119 (same as Lin) |

BRIEF DESCRIPTION OF THE FIGURES

FIG. 4 is a representation of the results of limiting dilution studies in table format.

DETAILED DESCRIPTION OF THE PREFERRED EMBODIMENTS

Figure 1:
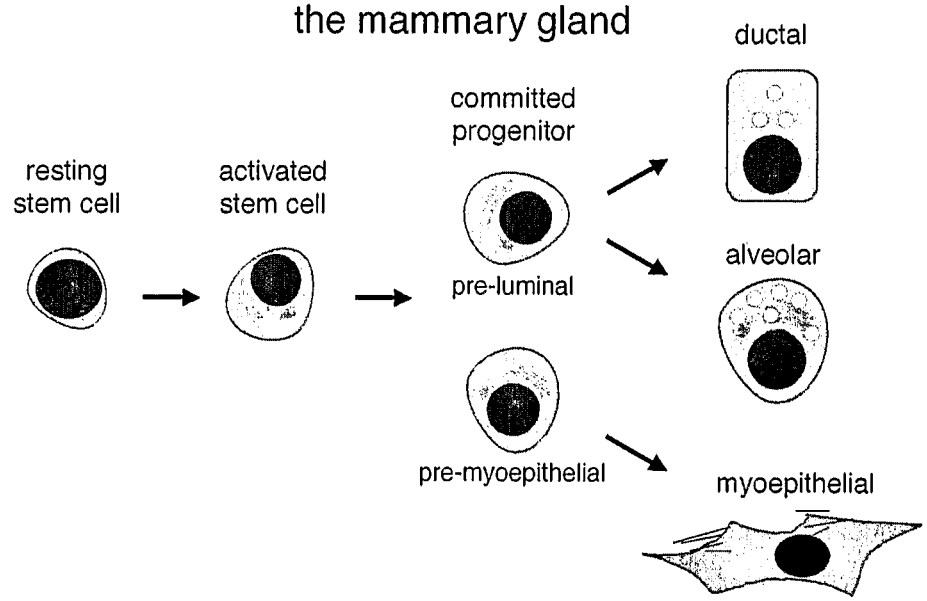
FIG. 1 is a schematic representation of the proposed model of mammary epithelial cell development.

In one embodiment, the present invention provides a method for isolating a substantially homogenous population of MaSCs from a biological sample said method comprising subjecting said biological sample to a tissue-disruption means to provide a heterogenous population of cells comprising the MaSCs to be isolated and subjecting said heterogenous population of cells to a cell surface marker discrimination means to isolate a substantially homogenous population of MaSCs.

Reference herein to a "population of cells" means two or more cells. A "substantially homogenous population" means a population comprising substantially of only one cell type. A "cell type" means a population of cells which are distinguished from other cells by a particular common characteristic. Preferably, the substantially homogenous population comprises a population of cells of which at least about 50% are of the same type, or at least about 60%, or at least about 70%, or at least about 80%, or at least about 90%, or at least about 95% or above such as at least about 100% are of the same type. Examples include 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% of cells of the same type.

The biological sample of the present invention may be derived from any organism such as a human, non-human primate (e.g. gorilla, macaque, marmoset), livestock animal (e.g. sheep, cow, horse, donkey, pig), companion animal (e.g. dog, cat), laboratory test animal (e.g. mouse, rabbit, rat, guinea pig, hamster), avian species, captive wild animal (e.g. fox, deer), reptile or amphibian (e.g. cane toad), fish (e.g. zebrafish) or any other organism (e.g. *C. elagans*).

Preferably, the biological sample of the present invention is derived from a human or mouse. Most preferably, the biological sample of the present invention is derived from a human.

Reference herein to "biological sample" is used in its broadest sense and means any sample, e.g. tissue, derived from a biological source such as, but not limited to, skin, muscle, neural, liver, kidney, eye, bone, fat, bone marrow, blood and mammary tissue. In a preferred embodiment the biological sample of the present invention is, or is derived from, mammary tissue.

Generally, the biological samples of the present invention are required to undergo disruption to produce single cells. This is referred to herein as "tissue-dissociation means". Reference herein to "tissue-disassociation means" means any method which dissociates tissue into single cells such as, but not limited to, mechanical and/or enzymatic treatment. Examples of such methods are trituration and treatment using trypsin, papain, neutral protease (dispase), chymotrypsin, elastase, collagenase and hyaluronidase. The dissociation of tissue may be performed by any method that is well known in the art.

Reference herein to "stem cell" means a cell which is capable of self-renewal and proliferation and which has the potential to generate a large repertoire of functional, differentiated progeny. The ability of a stem cell to self-renew itself is an essential aspect of the definition of a stem cell as used herein. Stem cells may divide asymmetrically, with one daughter retaining the stem cell state and the other daughter expressing a specific function and/or a phenotype distinct from the first mentioned daughter cell. Alternatively, some of the stem cells in a population can divide symmetrically into two stem cells, thus maintaining the same stem cells in the population as a whole, while other cells in the population give rise to differentiated progeny only. It is possible that cells that begin as stem cells might proceed towards a differentiated phenotype, but then reverse and re-express a stem cell phenotype. A stem cell is an operational term meaning a cell which can divide to produce another stem cell (i.e. has a self renewal capacity), as well as a cell which can differentiate along multiple specific differentiation paths. It is often the case that a particular cell with a differentiation lineage has derived from a less differentiated parent and can still divide and give rise to a more differentiated cellular progeny. Reference herein to a stem cell should also be taken to include reference to a "precursor cell" or "progenitor cell" or any other cell with stem cell characteristics.

The preferred stem cells of the present invention are MaSCs.

Accordingly, the present invention provides a method for isolating a substantially homogenous population of MaSCs from a biological sample said method comprising subjecting said biological sample to a tissue-disruption means to provide a heterogenous population of cells comprising the MaSCs to be isolated and subjecting said heterogenous population of cells to a cell surface marker discrimination means to isolate a substantially homogenous population of MaSCs.

Once the biological sample has been disassociated, the MaSCs are selected using various methods which utilize, for example, molecules capable of interacting with cell surface proteins i.e. cell surface protein interacting molecules. In these methods, the molecules capable of interacting with cell surface proteins selectively bind to proteins present on the surface of cells which comprise the MaSC population of interest. The bound cell surface protein interacting molecules then act as a flag to signal the identification of MaSCs. Selection methods include, for example, FACS and biotin-avidin or biotin-streptavidin separations which use solid supports, such as affinity column matrix or plastic surfaces, or magnetic beads.

A particularly preferred method of MaSC selection according to the present invention is FACS.

The cell surface protein interacting molecules contemplated by the present invention may interact with any protein present on the surface of MaSCs, including, but not limited to, one or more of the proteins Sca-1, CD44, CD49, Peanut agglutinin (PNA), CD71, CD45, TER119 (Lin), CD31, CD24 and CD29.

In a preferred embodiment, the cell surface protein interacting molecules contemplated by the present invention interact with one or more of the proteins CD71, CD45, TER119, CD31, CD24 and CD29 present on the cell surface of MaSCs.

In one preferred embodiment, the MaSCs selected by the method of the present invention produce low amounts of CD45, TER119 and CD31, i.e. $CD45^{lo}TER119^{lo}CD31^{lo}$, and high amounts of CD24 and CD29, i.e. $CD24^{hi}CD29^{hi}$. As such, the preferred MaSCs of the present invention are conveniently referred to as $CD45^{lo}TER119^{lo}CD31^{lo}CD24^{hi}CD29^{hi}$ MaSCs. The terms, "$TER119^{lo}$", "$Lin^-$" and "$Lin^{lo}$" are used interchangeably throughout the specification and refer to the same marker at low or zero levels.

Accordingly, the present invention provides a method for isolating a substantially homogenous population of $CD45^{lo}TER119^{lo}CD31^{lo}CD24^{hi}CD29^{hi}$ MaSCs from a biological sample said method comprising subjecting said biological sample to a tissue-disruption means to provide a heterogenous population of cells comprising the $CD45^{lo}TER119^{lo}CD31^{lo}CD24^{hi}CD29^{hi}$ MaSCs to be isolated and subjecting said heterogenous population of cells to a cell surface marker discrimination means to isolate a substantially homogenous population of $CD45^{lo}TER119^{lo}CD31^{lo}CD24^{hi}CD29^{hi}$ MaSCs.

The cell surface protein interacting molecules used for cell surface discrimination may be labeled with a fluorescent compound. When the fluorescently labeled antibody or molecule with selective binding capacity is exposed to light of the proper wavelength, its presence can then be detected due to fluorescence. Among the most commonly used fluorescent labeling compounds are fluorescein isothiocyanate (FITC), rhodamine isothiocyanate (RITC), phycoerythrin (PE), phycocyanin, allophycocyanin, o-phthaldehyde and fluorescamine. The antibody or molecule with selective binding capacity can also be detectably labeled using fluorescence emitting metals such as $^{152}Eu$ or others of the lanthanide series. These metals can be attached to the antibody or molecule with selective binding capacity using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody or molecule with selective binding capacity is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody or molecule with selective binding capacity of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. All such methods of labeling an antibody or a molecule with selective binding capacity are contemplated by the present invention.

The method of the present invention provides therefore MaSCs that are useful, inter alia, for tissue augmentation, replacing cells damaged by disease or injury and for identifying agents which modulate MaSC survival, self-renewal, proliferation and/or differentiation.

Accordingly, in another embodiment, the present invention provides a substantially homogenous population of MaSCs selected according to a method comprising subjecting said biological sample to a tissue-disruption means to provide a heterogenous population of cells comprising the $CD45^{lo}TER119^{lo}CD31^{lo}CD24^{hi}CD29^{hi}$ MaSCs to be isolated and subjecting said heterogenous population of cells to a cell surface marker discrimination means to isolate a substantially homogenous population of $CD45^{lo}TER119^{lo}CD31^{lo}CD24^{hi}CD29^{hi}$ MaSCs.

As stated hereinbefore, the present invention contemplates a method for cell replacement therapy in an organism, said method comprising generating a substantially homogenous population of $CD45^{lo}TER119^{lo}CD31^{lo}CD24^{hi}CD29^{hi}$ MaSCs isolated according to a method comprising subjecting a biological sample to a tissue-disruption means to provide a heterogenous population of cells comprising the $CD45^{lo}TER119^{lo}CD31^{lo}CD24^{hi}CD29^{hi}$ MaSCs to be isolated and subjecting said heterogenous population of cells to a cell surface marker discrimination means to isolate a substantially homogenous population of $CD45^{lo}TER119^{lo}CD31^{lo}CD24^{hi}CD29^{hi}$ MaSCs and introducing said homogenous population of MaSCs to said organism or an organism which is capable of receiving said MaSCs.

Reference herein to "cell replacement therapy" includes, in one form, a process in which undifferentiated cells are selected, optionally maintained in vitro and then eventually returned to the subject from which they were obtained, a compatible subject or an immunocompromised subject. While in vitro or in vivo, the cells may differentiate and proliferate into a particular cell lineage or into multiple cell lineages. Thus, cell replacement therapy requires that an undifferentiated cell appropriately differentiates for the purposes of providing repair, regeneration or replacement of a cell function including the replacement of an organ or a tissue. "Cell replacement therapy" also includes augmentation therapy. The organism into which the purified stem cells or their progeny are implanted for the purpose of "cell replacement therapy" or repair of tissue, or from which stem cells can be derived may be any organism such as a human, non-human primate (e.g. gorilla, macaque, marmoset), livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer), reptile or amphibian (e.g. cane toad), fish (e.g. zebrafish) or any other organism (e.g. *C. elagans*). Preferably the organism is a human or mouse. Most preferably the organism is a human.

Although generally the cells are returned to the same organism which they were derived from they may also be provided to another compatible organism or immunocompromised organism.

In another embodiment, the present invention provides a composition for use in cell replacement therapy, said composition comprising a substantially homogenous population of MaSCs selected according to a method comprising subjecting said biological sample to a tissue-disruption means to provide a heterogenous population of cells comprising the $CD45^{lo}TER119^{lo}CD31^{lo}CD24^{hi}CD29^{hi}$ MaSCs to be isolated and subjecting said heterogenous population of cells to a cell surface marker discrimination means to isolate a substantially homogenous population of $CD45^{lo}TER119^{lo}CD31^{lo}CD24^{hi}CD29^{hi}$ MaSCs.

The MaSCs for use in cell replacement therapy and compositions useful for same may also be genetically modified MaSCs. Reference herein to "genetically modified MaSCs" refers to MaSCs which have undergone some form of genetic manipulation such as introduction of DNA which encodes a sense or antisense mRNA or a ribozyme or RNAi or siRNA. The introduced nucleic acid molecule may target an endogenous gene for gene silencing or part of a gene or may introduce a new gene. The introduced nucleic acid may be introduced by a variety of techniques, including, but not limited to, calcium-phosphate-mediated transfection, DEAE-mediated transfection, microinjection, retroviral transformation, protoplast fusion and lipofection. The genetically modified cell may express the introduced nucleic acid in either a transient or long-term manner. In general, transient expression occurs when introduced DNA does not stably integrate into the chromosomal DNA of the transfected cell. In contrast, long-term expression of foreign DNA occurs when the foreign DNA has been stably integrated into the chromosomal DNA of the transfected cell. The introduced nucleic acid molecule may also be in the form of an artificial chromosome such as, with respect to humans, a human artificial chromosome (HAC).

As stated hereinbefore, the MaSCs of the present invention facilitate a method for identifying agents which modulate MaSC survival, self-renewal, proliferation and/or differentiation, both in vitro and/or in vivo. In particular, identifying agents which modulate the in vivo activity of MaSCs overcomes the need for invasive cell replacement therapy altogether.

Reference herein to an "agent" should be understood as a reference to any proteinaceous or non-proteinaceous molecule derived from natural, recombinant or synthetic sources. The term "agent" as used herein can be used interchangeably with other terms and phrases such as compound, agent, active agent, drug, pharmacologically active agent and medicament, or, with any other term that refers to a substance that induces a desired pharmacological and/or physiological effect. The terms also encompass pharmaceutically acceptable and pharmacologically active ingredients of those agents specifically mentioned herein including but not limited to salts, esters, amides, prodrugs, active metabolites, analogs and the like. When the terms compound, agent, active agent, drug, pharmacologically active agent and medicament are used, then it is to be understood that this includes the agent per se as well as pharmaceutically acceptable, pharmacologically active salts, esters, amides, prodrugs, metabolites, analogs, etc. The term agent is not to be construed as a chemical compound only but extends to peptides, polypeptides and proteins as well as genetic molecules such as RNA, DNA and chemical analogs thereof.

The present invention enables, therefore, screening for agents useful for modulating MaSC activities.

The steps involved generally comprise:
(i) selecting the MaSCs of the present invention;
(ii) placing aliquots of the selected MaSCs into suitable receptacles; and
(iii) exposing the aliquots of MaSCs to agents for a particular period of time and under particular conditions; and
(iv) screening for morphological, physiological and genetic changes to the MaSCs.

Morphological, physiological and genetic changes includes screening for states of survival, self-renewal, proliferation and/or differentiation.

Assays measuring differentiation include, for example, measuring cell surface protein markers associated with stage-specific expression of a tissue, enzymatic activity, functional activity or morphological changes (Watt, *FASEB* 5:281-284, 1991; Francis, *Differentiation* 57:63-75, 1994; Raes, *Adv Anim Cell Biol Technol Bioprocesses*, Butterworths, London, pp 161-171, 1989). Assays measuring cell proliferation or differentiation include, for example, chemosensitivity to neutral red dye (Cavanaugh et al., *Investigational New Drugs* 8:347-354. 1990), incorporation of radiolabeled nucleotides (Cook et al., *Anal Biochem* 179:1-7, 1989), incorporation of 5-bromo-2'-deoxyuridine (BrdU) in the DNA of proliferating cells (Porstmann et al., *J Immunol Methods* 82:169-179, 1985), and use of tetrazolium salts (Mosmann, *J Immunol Methods* 65: 55-63, 1983; Alley et al., *Cancel Res* 48: 589-601, 1988; Marshall et al., *Growth Reg* 5: 69-84, 1985; and Scudiero et al., *Cancer Res* 48: 4827-4833, 1988) and by measuring proliferation using $^3$H-thymidine uptake (Crowley et al. *J Immunol Methods* 133: 55-66, 1990).

Protein arrays provide a particularly useful way of screening for states of survival, self-renewal, proliferation and/or differentiation in MaSCs.

Alternatively, agents can be screened for alterations to genetic material in MaSCs. For example, micro- or macroarray analysis and/or techniques such as serial analysis of gene expression (SAGE), differential hybridization, differential PCR and substractive hybridization can be used, for example, to screen for transcripts present in proliferating and/or differentiating cells compared to resting MaSCs. Once identified, the corresponding genes become specific targets for expression modulating agents to either facilitate and inhibit expression. Alternatively, MaSCs are exposed to potential agents and the changes in expression of genetic material monitored using, for example, differential expression protocols. The aim is to first find an agent which up- or down-regulates genetic material in a MaSC and then determine whether this impacts on MaSC survival, self-renewal, proliferation and/or differentiation.

Screening for modulatory agents according to the invention can be achieved by any suitable method. For example, as described hereinbefore, the method may include contacting a MaSC with a test compound (i.e. a putative modulatory agent) and screening for the modulation of the level and/or functional activity of a protein encoded by a polynucleotide (this includes proteomics), or the modulation of the level of an expression product encoded by a polynucleotide, or the modulation of the activity or expression of a downstream cellular target of a protein or of an expression product or for a raft of physiological, biochemical, immunological or genetic changes including changes in surface antigen profiles (e.g. changes in CD antigen profile). Detecting such modulation can be achieved utilizing techniques including, but not restricted to, ELISA, cell-based ELISA, filter-binding ELISA, inhibition ELISA, Western blots, immunoprecipitation, slot or dot blot assays, immunostaining, RIA, scintillation proximity assays, fluorescent immunoassays using antigen-binding molecule conjugates or antigen conjugates of fluorescent substances such as fluorescein or rhodamine, Ouchterlony double diffusion analysis, immunoassays employing an avidin-biotin or a streptavidin-biotin detection system, and nucleic acid detection assays including reverse transcriptase polymerase chain reaction (RT-PCR).

The present invention, therefore, provides screening methods capable of identifying agents which are capable of inducing or inhibiting MaSC survival, self-renewal, proliferation and/or differentiation. In addition, the assays may detect the presence of increased or decreased expression of genes or production of proteins on the basis of increased or decreased mRNA expression (using, for example, the nucleic acid probes), increased or decreased levels of protein products (using, for example, antigen-binding molecules) or increased or decreased levels of expression of a reporter gene (e.g. GFP, β-galactosidase or luciferase) operably linked to a target molecule-related gene regulatory region in a recombinant construct.

Thus, for example, MaSCs which may be cultured or maintained in a particular target medium and a test compound added to the culture medium. After allowing a sufficient period of time (e.g. 1-200 hours) for the compound to induce or inhibit a physiological, biochemical, immunological or morphogical changes, any change from an established baseline may be detected using any of a range of macroscopic, microsopic techniques described above and well known in the art. Using the nucleic acid probes and/or antigen-binding molecules for example, detection of changes in genetic expression or surface antigens can be readily detected.

In yet another embodiment, random peptide libraries consisting of all possible combinations of amino acids attached to a solid phase support may be used to identify peptides that are able to bind to a particular MaSC surface antigen (which is indicative of a particular stage of development). The target antigen may be purified, recombinantly expressed or synthesized by any suitable technique. Such molecules may be conveniently prepared by a person skilled in the art using standard protocols as, for example, described in Sambrook, et al. (*A Molecular Cloning—A Laboratory Manual*, Cold Spring Harbour, New York, USA, 1989, in particular, Sections 16 and 17) and Ausubel et al., ("Current Protocols in Molecular Biology" John Wiley & Sons Inc, 1994-1998, in particular Chapters 10 and 16). Alternatively, a target antigen according to the invention may be synthesized using solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications and in Roberge et al. (*Science* 269: 202, 1995).

To identify and isolate the peptide/solid phase support that interacts and forms a complex with a target antigen, it may be necessary to label or "tag" the target antigen. The target polypeptide may be conjugated to any suitable reporter molecule, including enzymes such as alkaline phosphatase and horseradish peroxidase and fluorescent reporter molecules such as FITC, rhodamine and PE. Conjugation of any given reporter molecule, with target antigen, may be performed using techniques that are routine in the art. Alternatively, target antigen expression vectors may be engineered to express a chimeric target antigen containing an epitope for which a commercially available antigen-binding molecule exists. The epitope specific antigen-binding molecule may be tagged using methods well known in the art including labeling with enzymes, fluorescent dyes or colored or magnetic beads.

For example, the "tagged" target antigen conjugate is incubated with the random peptide library for 30 minutes to one hour at 22° C. to allow complex formation between target antigen and peptide species within the library. The library is then washed to remove any unbound target antigen. If the target antigen has been conjugated to alkaline phosphatase or horseradish peroxidase, the whole library is poured into a petri dish containing a substrate for either alkaline phosphatase or peroxidase, for example, 5-bromo-4-chloro-3-indoyl phosphate (BCIP) or 3,3',4,4"-diaminobenzidine (DAB), respectively. After incubating for several minutes, the peptide/solid phase-target polypeptide complex changes color, and can be easily identified and isolated physically under a dissecting microscope with a micromanipulator. If a fluorescently tagged target polypeptide has been used, complexes may be isolated by fluorescent activated sorting. If a chimeric target polypeptide having a heterologous epitope has been used, detection of the peptide/target polypeptide complex may be accomplished by using a labeled epitope specific antigen-binding molecule. Once isolated, the identity of the peptide attached to the solid phase support may be determined by peptide sequencing.

The identification of agents capable of modulating MaSC activities enables the production of pharmaceutical compositions for use in the therapeutic treatment of a range of diseases, conditions and/or injuries which require cell replacement therapy or the modulation of MaSC activities in vivo.

Reference herein to "treatment" may mean a reduction in the severity of an existing condition in a subject. The term "treatment" is also taken to encompass "prophylactic treatment" to prevent the onset of a condition in a subject. The term "treatment" does not necessarily imply that a subject is treated until total recovery. Similarly, "prophylactic treatment" does not necessarily mean that the subject will not eventually contract a condition.

Subject as used herein refers to humans and non-human primates (e.g. gorilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer), reptiles or amphibians (e.g. cane toad), fish (e.g. zebrafish) and any other organisms (e.g. *C. elagans*) who can benefit from the modulatory agents of the present invention.

There is no limitation on the type of organism that could benefit from the presently described modulatory agents, including those organisms into which MaSCs may have been introduced.

The most preferred subject of the present invention is a human.

A subject regardless of whether it is a human or non-human organism may be referred to as a patient, individual, animal, host or recipient.

The MaSC modulatory agents of the present invention can be combined with one or more pharmaceutically acceptable carriers and/or diluents to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., Remington's Pharmaceutical Sciences, 18$^{th}$ Edition, Mack Publishing Company, Easton, Pa., 1990 ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the modulatory agent of the invention and on its particular physio-chemical characteristics. Administration of the agent, in the form of a pharmaceutical composition, may be performed by any convenient means known to one skilled in the art. Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, patch and implant.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier, see, e.g., International Patent Publication Number WO 96/11698.

Agents of the present invention, when administered orally, may be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g. Fix, *Pharm Res* 13:1760-1764, 1996; Samanen et al., *J Pharm Pharmacol* 48:119-135, 1996; U.S. Pat. No. 5,391,377, describing lipid compositions for oral delivery of therapeutic agents (liposomal delivery is discussed in further detail, infra).

The pharmaceutical forms suitable for injectable use include sterile aqueous solutions (where water-soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the agents in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

For parenteral administration, the agent may dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the agents are being administered intrathecally, they may also be dissolved in cerebrospinal fluid.

For transmucosal or transdermal administration, penetrants appropriate to the barrier to be permeated can be used for delivering the agent. Such penetrants are generally known in the art e.g. for transmucosal administration, bile salts and fusidic acid derivatives. In addition, detergents can be used to facilitate permeation. Transmucosal administration can be through nasal sprays or using suppositories e.g. Sayani and Chien, *Crit Rev Ther Drug Carrier Syst* 13:85-184, 1996. For topical, transdermal administration, the agents are formulated into ointments, creams, salves, powders and gels. Transdermal delivery systems can also include patches.

For inhalation, the agents of the invention can be delivered using any system known in the art, including dry powder aerosols, liquids delivery systems, air jet nebulizers, propellant systems, and the like, see, e.g., Patton, *Nat Biotech* 16:141-143, 1998; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, for example, air jet nebulizers.

The agents of the invention can also be administered in sustained delivery or sustained release mechanisms, which can deliver the formulation internally. For example, biodegradeable microspheres or capsules or other biodegradeable polymer configurations capable of sustained delivery of a peptide can be included in the formulations of the invention (e.g. Putney and Burke, *Nat Biotech* 16:153-157, 1998).

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's, Chapters 37-39.

In one aspect, the pharmaceutical formulations comprising agents of the present invention are incorporated in lipid monolayers or bilayers such as liposomes, see, e.g., U.S. Pat. Nos. 6,110,490; 6,096,716; 5,283,185 and 5,279,833. The invention also provides formulations in which water-soluble modulatory agents of the invention have been attached to the surface of the monolayer or bilayer. For example, peptides can be attached to hydrazide-PEG-(distearoylphosphatidyl)

ethanolamine-containing liposomes (e.g. Zalipsky et al., *Bioconjug Chem* 6:705-708, 1995). Liposomes or any form of lipid membrane, such as planar lipid membranes or the cell membrane of an intact cell e.g. a red blood cell, can be used. Liposomal formulations can be by any means, including administration intravenously, transdermally (Vutla et al., *J Pharm Sci* 85:5-8, 1996), transmucosally, or orally. The invention also provides pharmaceutical preparations in which the nucleic acid, peptides and/or polypeptides of the invention are incorporated within micelles and/or liposomes (Suntres and Shek, *J Pharm Pharmacol* 46:23-28, 1994; Woodle et al., *Pharm Res* 9:260-265, 1992). Liposomes and liposomal formulations can be prepared according to standard methods and are also well known in the art see, e.g., Remington's; Akimaru et al., *Cytokines Mol Ther* 1:197-210, 1995; Alving et al., *Immunol Rev* 145:5-31, 1995; Szoka and Papahadjopoulos, *Ann Rev Biophys Bioeng* 9:467-508, 1980, U.S. Pat. Nos. 4,235,871, 4,501,728 and 4,837,028.

The pharmaceutical compositions of the invention can be administered in a variety of unit dosage forms depending upon the method of administration. Dosages for typical modulatory pharmaceutical compositions are well known to those of skill in the art. Such dosages are typically advisorial in nature and are adjusted depending on the particular therapeutic context, patient tolerance, etc. The amount of modulatory agent adequate to accomplish this is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the phaimacokinetics, i.e., the pharmaceutical composition's rate of absorption, bioavailability, metabolism, clearance, and the like. See, e.g., Remington's; Egleton and Davis, *Peptides* 18:1431-1439, 1997; Langer, *Science* 249:1527-1533, 1990.

In accordance with these methods, the agents and/or pharmaceutical compositions defined in accordance with the present invention may be co-administered with one or more other agents. By "co-administered" is meant simultaneous administration in the same formulation or in two different formulations via the same or different routes or sequential administration by the same or different routes. By "sequential" administration is meant a time difference of from seconds, minutes, hours or days between the administration of the two types of modulatory agents and/or pharmaceutical compositions. Co-administration of the modulatory agents and/or pharmaceutical compositions may occur in any order.

Alternatively, targeting therapies may be used to deliver the active agent more specifically to certain types of cell, by the use of targeting systems such as antibodies or cell specific ligands or specific nucleic acid molecules. Targeting may be desirable for a variety of reasons, e.g. if the agent is unacceptably toxic or if it would otherwise require too high a dosage or if it would not otherwise be able to enter the target cells.

Instead of administering the agents directly, they could be produced in the target cell, e.g. in a viral vector such as described above or in a cell based delivery system such as described in U.S. Pat. No. 5,550,050 and International Patent Publication Numbers WO 92/19195, WO 94/25503, WO 95/01203, WO 95/05452, WO 96/02286, WO 96/02646, WO 96/40871, WO 96/40959 and WO 97/12635. The vector could be targeted to the target cells. The cell based delivery system is designed to be implanted in a patient's body at the desired target site and contains a coding sequence for the target agent. Alternatively, the agent could be administered in a precursor form for conversion to the active form by an activating agent produced in, or targeted to, the cells to be treated. See, for example, European Patent Application Number 0 425 731A and International Patent Publication Number WO 90/07936.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The present invention is further described by the following non-limiting examples.

Example 1

General Experimental Procedures

Mammary Cell Preparation

Figure 2:
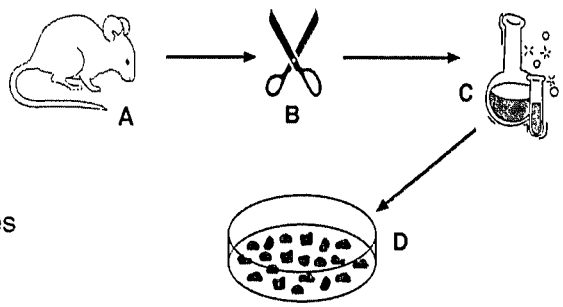
FIG. 2 is a schematic representation of the protocol for mammary epithelial cell preparation.

The nature of mouse mammary epithelial stem cells was evaluated using the in vivo mammary epithelial cell transplantation approach described in Alvi et al., *Breast Cancer Res* 5:R1-R8, 2003. The protocol for mammary epithelial cell purification was optimised and is summarized in FIG. 2. It initially involved the harvesting of the $3^{rd}$, $4^{th}$ (after first removing the visible lymph node) and $5^{th}$ mammary glands from eight-week-old mice. The harvested glands were mechanically dissociated using a McIllwain tissue chopper and then enzymatically disrupted with 300 U/ml collagenase and 100 U/ml hyaluronidase in dissociation medium (DME-HAM, 5% v/v FCS, 5 µg/ml insulin, 500 ng/ml hydrocortisone 10 ng/ml EGF and 20 ng/ml cholera toxin) for one hour at 37° C., with forceful titurations every 20 minutes. The resulting organoid suspension was serially treated with 0.25% w/v trypsin/1 mM EGTA for 1-2 minutes at 37° C. to disrupt cell-cell interactions, 5 mg/ml dispase and DNAse for 5 minutes at 37° C. to break down basement membrane components and disaggregate clumped DNA, and 0.8% w/v $NH_4Cl$/1 mM EDTA for 1-2 minutes at room temperature to reduce red blood cell contamination. The resultant suspension was finally passed through a 40 µm filter to remove any residual large cell aggregates, and the number of non-red blood cells determined by counting on a haemocytometer.

Cell suspensions were then blocked with rat immunoglobulin and anti-Fc receptor antibody, prior to immunostaining with other antibodies specific for certain cell surface molecules. To enable identification and FACS-purification of phenotypically distinct cell populations, these antibodies were conjugated to fluorescent markers. Flow cytometric analysis of the immunostained cell population was then performed, and cell populations of interest purified by FACS. After sorting, the purified cells were prepared for transplantation by resuspending them at the desired concentration in a balanced salt solution with 2% v/v FCS and 10% w/v trypan blue.

In a slight alternative to the method above, mammary glands were dissected from 8-week old female mice. After mechanical dissociation with a McIlwain tissue chopper (The Mickle Laboratory Engineering Co. Ltd., Guildford, UK), the tissue was placed in culture medium (CM) (DME HAM with 1 mM glutamine, 5 µg/ml insulin, 500 ng/ml hydrocortisone, 10 ng/ml EGF and 20 ng/ml cholera toxin supplemented with 5% v/v bovine calf serum (BCS)) containing 300 U/ml collagenase (Sigma, St Louis, USA) and 100 U/ml hyaluronidase (Sigma), and digested for 1 hour at 37° C. The resultant organoid suspension was sequentially resuspended in 0.25% w/v trypsin-EGTA for 1-2 min, 5 mg/ml dispase (Roche Diagnostics, Indianapolis, USA) and 0.1 mg/ml DNase (Worthington, Lakewood, USA) for 5 min, and 0.8% w/v $NH_4Cl$ for 3 min prior to filtration and labelling.

Cell Labelling, Flow Cytometry and Sorting

Hoechst staining was performed for 1 hour at 37° C. with 6 µg/ml $Hoechst_{33342}$ (Sigma). Blocking was performed in rat γ globulin (Jackson Laboratories, West Grove, USA) and anti-CD16/CD32 Fcγ III/II receptor antibody (BD Pharmingen, San Diego, USA) for 10 min. Antibody incubations were performed at 4° C. for 25 min. Antibodies against mouse antigens were purchased from BD Pharmingen unless otherwise specified, and included CD24-PE, biotinylated and APC-conjugated CD31, biotinylated and APC-conjugated CD45, biotinylated TER119, Sca-1-FITC and -PE, CD29-FITC (Chemicon Europe, Hampshire, UK), and anti-milk (Nordic Immunological Laboratories, Tilburg, Netherlands). Streptavidin-APC was purchased from BD Pharmingen. Fluorochrome-conjugated secondary antibodies included anti-rabbit Ig-$Alexa_{594}$ and -$Alexa_{488}$ (Molecular Probes, Eugene, USA). Cells were resuspended in 0.5 µg/ml propidium iodide (Sigma) prior to analysis. Data analysis was performed on the single, live cell gate using WEASEL software (http://www.wehi.edu.au/cytometry/WEASELv2.html). Cell sorting was carried out on a FACS-DiVa, FACStar or FACS Vantage cell sorter (Becton Dickinson, Mountain View, Calif.). The purity of sorted populations was routinely more than 95%.

MFP Transplantation Technique

Figure 3:
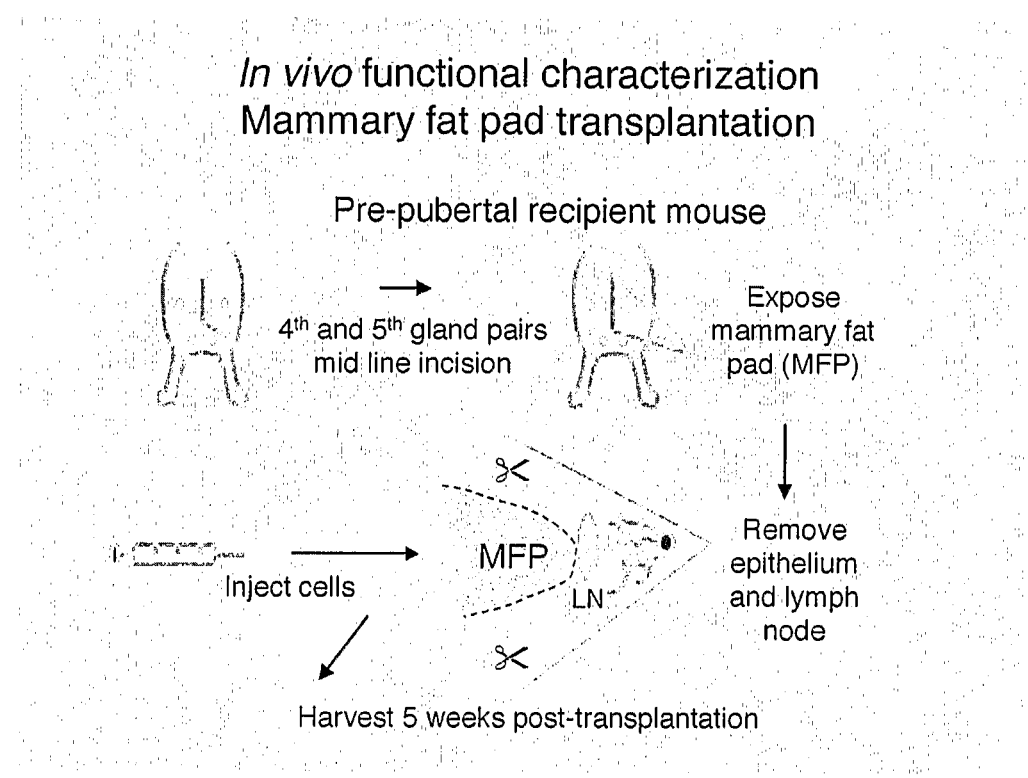
FIG. 3 is a schematic representation of the method for in vivo transplantation studies.

The MFP transplantation technique used in this investigation is summarized in FIG. 3. It was developed by DeOme et al., Cancer Res 19:515-520, 1959, and later adapted for transplantation of cell suspensions. The $4^{th}$ mammary gland of a syngeneic, pre-pubertal, three-week-old female mouse was exposed via an "inverted Y" incision, and the epithelialized portion of the gland, between the nipple and lymph node, removed by cautery and excision. The residual, de-epithelialized stromal tissue, the MFP, was then dissected off the subcutaneous tissue and folded back onto the peritoneum, remaining attached dorsally. Finally, a 10 µL volume of cell suspension was injected into the MFP via a Hamilton's syringe using a 30G needle. The presence of the injected cell suspension in the MFP was confirmed by the appearance of a blue bleb, due to the trypan blue present in the suspension. The technical quality of the injection was recorded, and any inadequate injections were excluded from the analysis, unless an epithelial outgrowth resulted from them. Five weeks after transplantation the mouse was killed, and the recipient MFPs wholemounted and fixed in Carnoys solution. They were then stained with haemotoxylin and evaluated microscopically. Only epithelial outgrowths that had both ductal and lobular elements were deemed to be positive.

Mice

FVB/NJ, C57BL/6, Rosa-$26^{15}$ (C57BL/6 backcross), MMTV-Wnt-1 (BALB/c backcross), and MMTV-neu (FVB/NJ backcross) mice were bred and maintained in an animal facility.

Mammary Fat Pad Transplantation and Analysis

Sorted cells were resuspended in PBS with 0.04% w/v trypan blue (Sigma) and 50% v/v fetal calf serum (FCS), and injected in 10 µl volumes into the inguinal glands of 3 week old female mice that had been cleared of endogenous epithelium. Visualization of cells prior to transplantation was performed in 10 µl Terasaki wells. Recipient glands were removed for evaluation after 5-10 weeks. Wild-type mammary outgrowths were stained with haematoxylin. $LacZ^+$ outgrowths were detected by X-gal staining for 36-48 hours. An outgrowth was defined as an epithelial structure comprising ducts arising from a central point, with lobules and/or terminal end buds. For secondary transplants, $LacZ^+$ cell suspensions from primary recipient glands were identified by PCR of genomic DNA.

In Vitro Assays

For colony assays, cells were sorted directly into the wells of 24-well plates containing CM with 0.1% w/v bovine serum albumin (BSA) in the presence of 10,000/$cm^2$ irradiated NIH-3T3 cells. The media was replaced with serum-free media after 24 hours, and 5 days later the colonies were fixed with methanol:acetone (1:1), stained with Giemsa, and counted. For three-dimensional assays, cells were resuspended in chilled 100% w/v Matrigel and the gels allowed to set prior to covering with serum-free medium as above. After 1 week, the medium was changed to DME-HAM containing 1 mM glutamine, 5 µg/ml insulin, 500 ng/ml hydrocortisone and 5 µg/ml prolactin, and the cells cultured for 2 weeks prior to fixation in 4% v/v paraformaldehyde, dehydration in 70% v/v ethanol, and embedding in paraffin for sectioning.

Immunostaining

Frozen sections were prepared from tissues embedded in OCT. After fixation in 100% v/v acetone, sections were rehydrated and blocked with 5% v/v BCS in PBS. Paraffin-embedded sections were dewaxed, washed in PBS, and subjected to antigen retrieval by boiling in 10 mM citrate buffer for 20 min and treatment with 150 mM glycine for 15 min, prior to blocking as above. Primary antibody staining was performed overnight at 4° C., while secondary antibody staining was performed for 30 min at room temperature and DAPI staining for 5 min at room temperature. Sections were imaged on a Leica TCS4 SP2 spectral confocal scanner linked to a Leica DMIRE2 inverted microscope.

Example 2

Limiting Dilution Studies

To establish the frequency of mammary stem cells in a cell population, limiting dilution analysis of mammary repopulating capacity was performed. Limiting dilution analysis is a well-established method for determining the frequency of cells in a specific population that have a certain characteristic (in our case, the ability to form a mammary epithelial structure in vivo). It assumes that the cells in question have this characteristic independent of other cells in the suspension. In our method, decreasing numbers of cells transplanted should produce a progressively smaller proportion of positive outgrowths, such that there is a linear relationship between the log of the number of cells transplanted and the proportion of positive outgrowths. Statistical analysis of our repopulation data was performed using L-Calc software (Stem Cell Technologies, Vancouver, Canada).

The mammary repopulating cell frequency in the overall cell population was analyzed, after first depleting it of contaminating haematopoietic cells, using the pan-leukocytic marker CD45 and the erythroid marker TER119, and non-viable cells as determined by propidium iodide (PI) uptake. Using freshly prepared cells that were not subjected to overnight or prolonged culture, the repopulating frequency of viable $CD45^{lo}TER119^{lo}$ cells was found to be approximately 1/3000 (FIG. 4). Similar repopulating frequencies were noted between FVB and C57Bl/6 animals. Control transplants with $CD45^{hi}TER119^{hi}$ cells at calculated limiting dilution did not produce any outgrowths. All subsequent analyses refer to the gated viable CD45$^{lo}$TER119$^{lo}$ cell population.

Example 3

Figure 5:
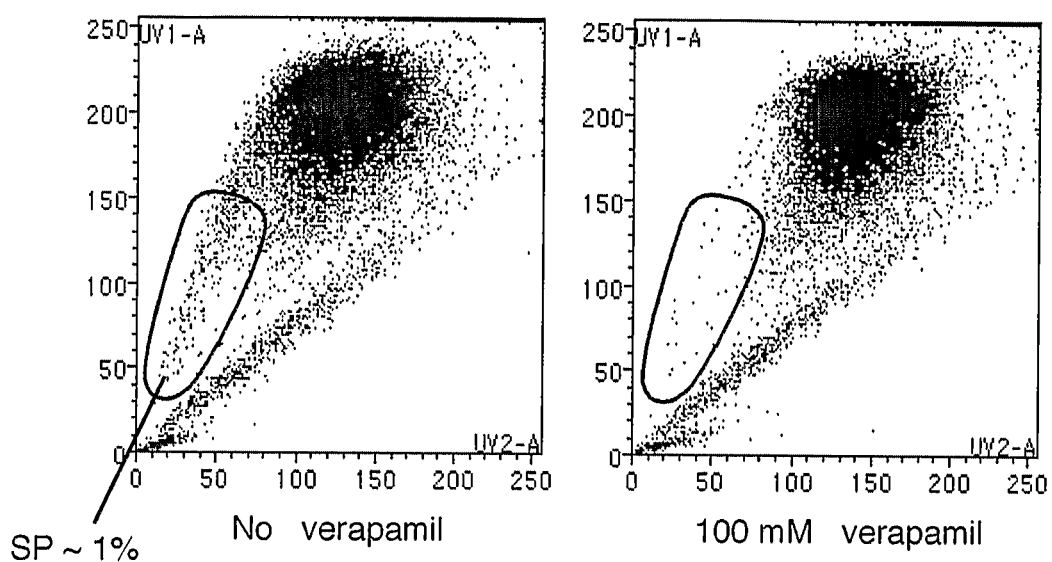
FIG. 5 is a graphical representation of the results of flow cytometric analysis of mammary cell preparation stained with Hoechst$_{33342}$.

Flow Cytometric Analysis of Mammary Cell Preparation Stained with Hoechst$_{33342}$ SP cells were identified in our freshly isolated mammary epithelial cell preparation using the Ho dye efflux assay. Prior to antibody staining, Ho dye was added to the cells at a concentration of 3 mg/mL and incubated at 37° C. for one hour. The presence of SP cells was confirmed by treatment of cells with verapamil, which has been shown to inhibit the BCRP1/ABCG2 membrane transporter pump responsible for the efflux of Hoechst dye. SP cells accounted for approximately 1% of the cells in our mammary cell preparation (FIG. 5).

Example 4

Repopulating Cell Frequency of SP and MP Cells

Figure 6:
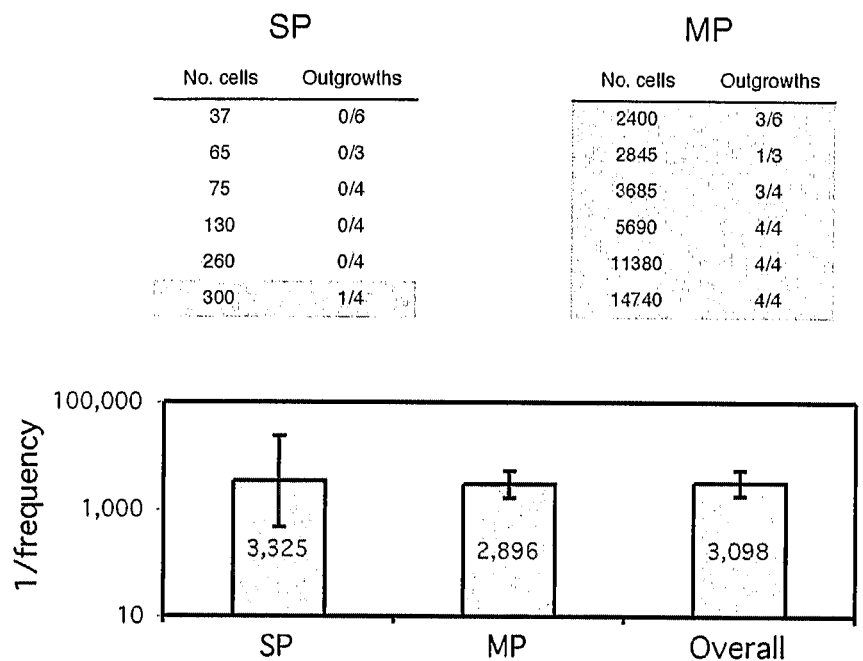
FIG. 6 is a graphical and tabular representation of the repopulating cell frequency of SP and MP cells. The tables show raw population data. The histograms show results of L-Calc analysis. Error bars represent 95% confidence intervals.

To determine whether SP cells are enriched for mammary repopulating capacity compared to main population (MP) cells, proportions of purified SP and MP cells were transplanted into the cleared fat pads of mice in limiting dilution studies. Since SP cells comprise no more than 1% of total gated cells, it would be anticipated that at least 100-fold fewer SP cells than MP cells would be required to reconstitute a mammary gland. Only 1 of 25 SP transplantations resulted in mammary gland outgrowths. In contrast, when proportionally equivalent MP cells were transplanted, 19/25 outgrowths were observed. Using L-Calc software, the frequency of repopulating cells within both SP and MP was determined to be approximately 1/3,000. No enrichment of mammary repopulating capacity was observed in the SP cells. Importantly, a corollary to this observation is that depletion of SP cells from the overall population did not compromise the repopulating capacity of the remaining cells in the MP. (FIG. 6). Thus, mammary SP cells do not appear to be enriched for mammary stem cells.

Example 5

Flow Cytometric Analysis of a Number of Cell Surface Makers

Figure 7:
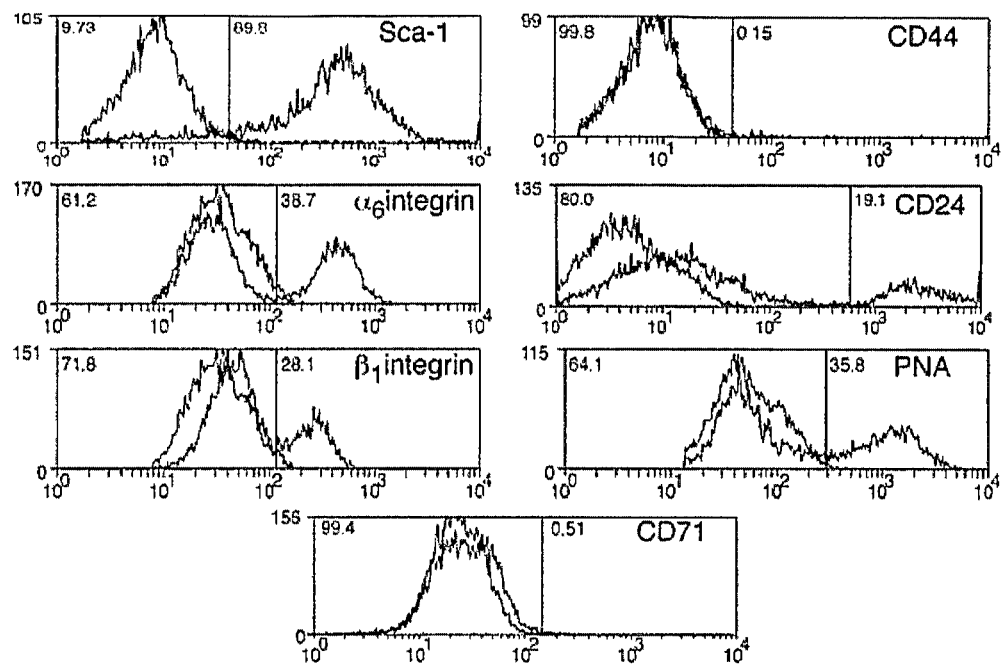
FIG. 7 is a graphical representation of flow cytometric analysis of a number of cell surface markers. Unshaded curves represent isotype-stained controls.
Figure 11:
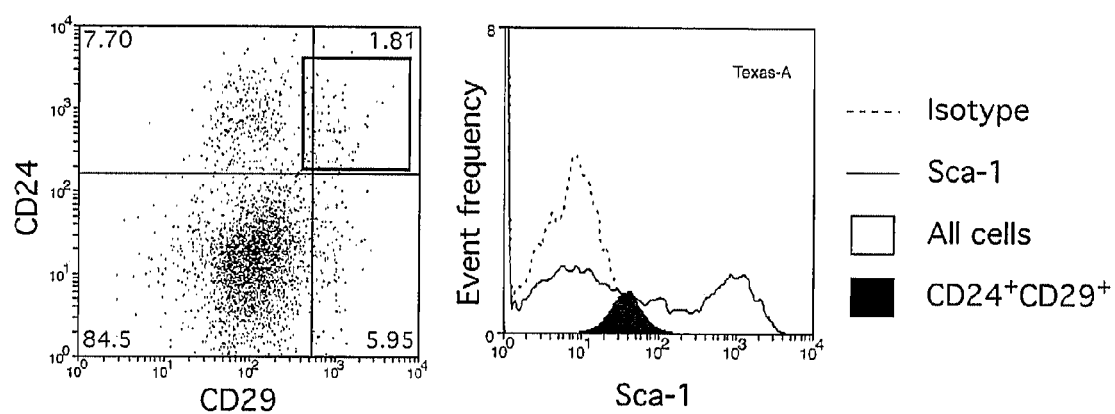
FIG. 11 is a graphical representation of flow cytometric analysis of CD45$^{lo}$TER$^{lo}$CD31$^{lo}$ cells triple stained with CD29, CD24 and Sca-1.

The presence of several other cell surface markers in mouse mammary epithelial cells was examined (FIG. 7). In contrast to previous published work (Welm et al., *Dev Biol* 245:42-56, 2002), we found that the majority of cells in our preparation expressed Sca-1. Subsequent analyses showed a reduced percentage of Sca-1$^{hi}$ cells after depletion of endothelial cells with CD31, though still in excess of expected (FIG. 11). Two-dimensional analyses showed significant co-expression of CD29/β$_1$-integrin, CD49f/α$_6$-integrin, and PNA (data not shown). A rhodamine$_{123}$$^{lo}$ or c-kit$^{hi}$ population, previously described in haematopoietic stem cells, was not detected (data not shown).

Example 6

Four Distinct Populations are Present

Figure 8:
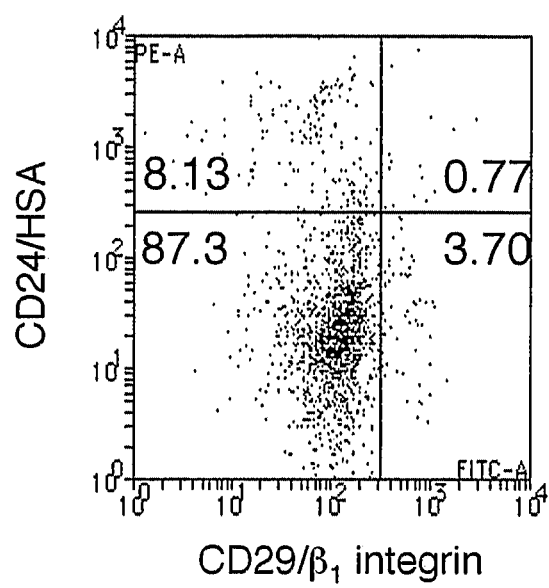
FIG. 8 is a graphical representation of flow cytometric analysis of CD45$^{lo}$TER$^{lo}$CD31$^{lo}$ cells co-stained with CD29-FITC and CD24-HSA.

Staining of CD45$^{lo}$Ter119$^{lo}$CD31$^{lo}$ cells with the cell surface markers CD24/HSA and CD29/β$_1$-integrin revealed four distinct populations (FIG. 8). CD24$^{hi}$CD29$^{hi}$ cells comprised approximately 0.8% of CD45$^{lo}$Ter119$^{lo}$CD31$^{lo}$ cells, compared to CD24$^{lo}$CD29$^{lo}$, which contained the majority (87%) of mammary cells. CD24$^+$CD29$^-$ and CD24$^-$CD29$^+$ cells accounted for 8.1 and 3.7% of CD45$^{lo}$Ter119$^{lo}$CD31$^{lo}$ cells respectively.

Example 7

Repopulating Cell Frequency of SP and MP Cells

Figure 9:
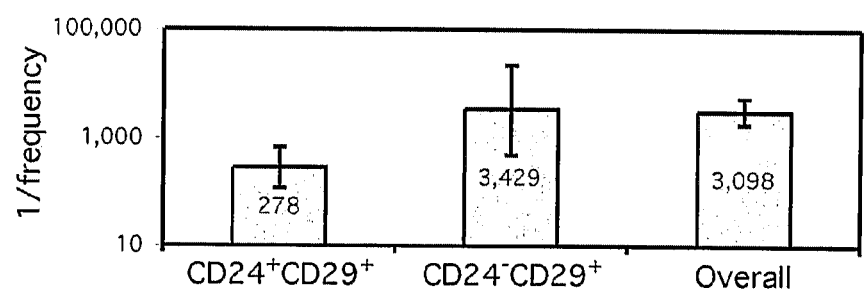
FIG. 9 is a graphical and tabular representation of the repopulating cell frequency of SP and MP cells. The tables show raw population data. The histograms show results of L-Calc analysis. Error bars represent 95% confidence intervals.
Figure 10:
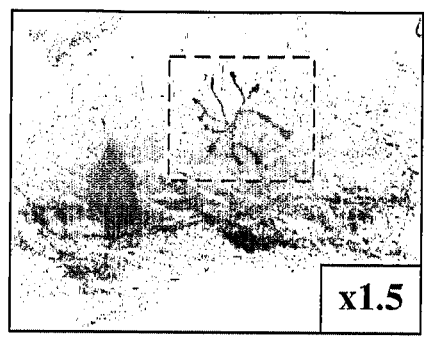
FIG. 10 is a photographical representation of wholemount analysis of recipient MFPs. It shows a typical outgrowth from transplanted CD24$^{hi}$CD29$^{hi}$ cells (upper left, enlarged lower left), in contrast to an empty MFP arising from transplanted CD24$^{hi}$CD29$^{lo}$ cells (upper right).
Figure 10:
Figure 10:
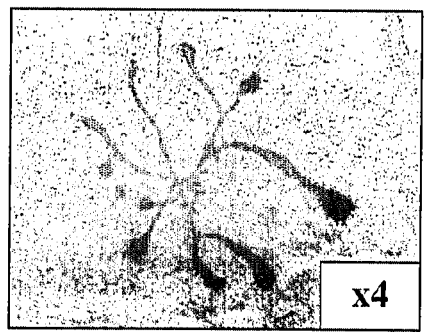

Transplantation of the four purified populations at limiting dilution revealed a substantial enrichment for repopulating cells within the CD24$^{hi}$CD29$^{hi}$ subpopulation (FIG. 9). For example in one experiment 100 CD24$^{hi}$CD29$^{hi}$ cells were sufficient to result in mammary outgrowths in 3/11 recipient glands (FIG. 10). In another experiment, 2/7 animals transplanted with 60 CD24$^{hi}$CD29$^{hi}$ cells developed mammary outgrowths, whereas none were detected in the three other populations. An L-Calc analysis, using data derived from the three independent experiments shown in FIG. 9, indicated that the repopulating cell frequency of the CD24$^{hi}$CD29$^{hi}$ population was 1/278. Another experiment, not included in the above analysis but nevertheless supportive of the findings, further divided the CD24$^{hi}$CD29$^{hi}$ cells according to Ho dye efflux capability. In this experiment, 3/4 MFPs transplanted with CD24$^{hi}$CD29$^{hi}$ MP cells developed outgrowths. The CD24$^{hi}$CD29$^{hi}$ population, which accounts for less than 1% of mammary epithelial cells (defined by CD45$^{lo}$Ter119$^{lo}$CD31$^{lo}$ staining), is thus approximately ten-fold enriched for repopulating cells compared to the overall population and we believe contains mammary stem cells.

Example 8

Flow Cytometric Analysis of CD45$^{lo}$TER$^{lo}$CD31$^{lo}$ Cells Triple-Stained with CD29, CD24 and Sca-1

Figure 12:
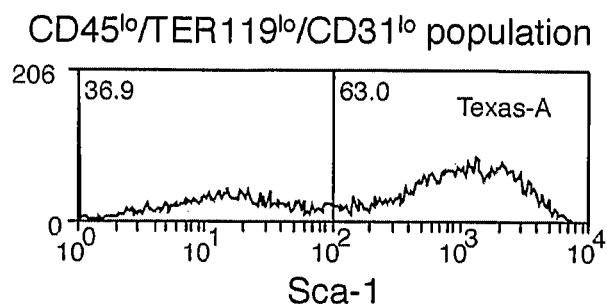
FIG. 12 is a graphical and tabular representation of the results of MFP transplantation experiments comparing the repopulating ability of cells with different Sca-1 expression levels (Sca-1$^{lo}$ versus Sca-1$^{hi}$).

CD24$^{hi}$CD29$^{hi}$ cells were also evaluated for Sca-1 expression, using triple staining with an Alexa$_{594}$-conjugated antibody. Sca-1 expression was found to be low (though not absent) in the CD24$^{hi}$CD29$^{hi}$ population, which appears to be enriched for repopulating cells, were found to be Sca-1$^{lo}$ (FIG. 11). Furthermore, two independent transplantation experiments comparing the repopulating capacity of Sca-1$^{hi}$ and Sca-1$^{lo}$ cells yielded no outgrowths derived from Sca$^{hi}$ cells, whereas outgrowths arose in glands transplanted with Sca-1$^{lo}$ cells (FIG. 12). Thus, this data suggests that Sca-1 does not represent a marker that enriches for mammary epithelial stem cells.

Example 9

Short Term Culture

Figure 13:
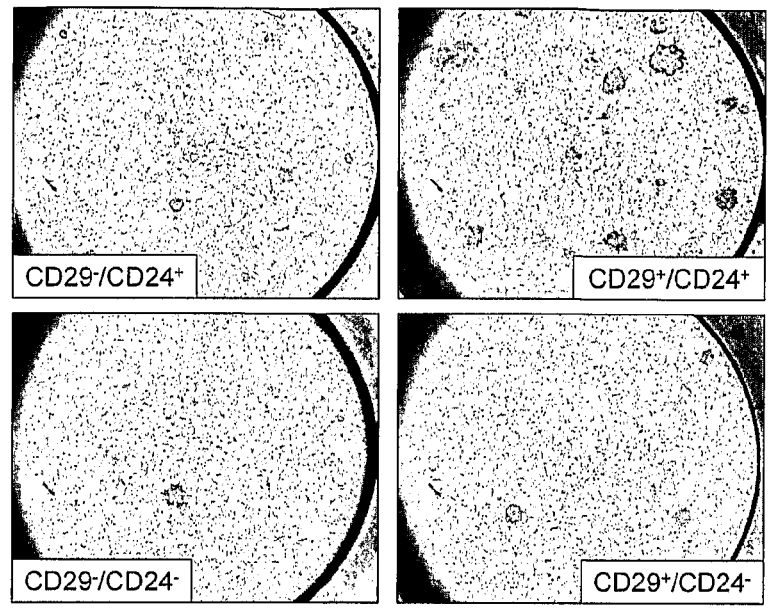
FIG. 13 is a photographic and tabular representation CD45$^{lo}$Ter119$^{lo}$CD31$^{lo}$ cells sorted by CD24 and CD29 staining to grow in short-term culture.
Figure 13:
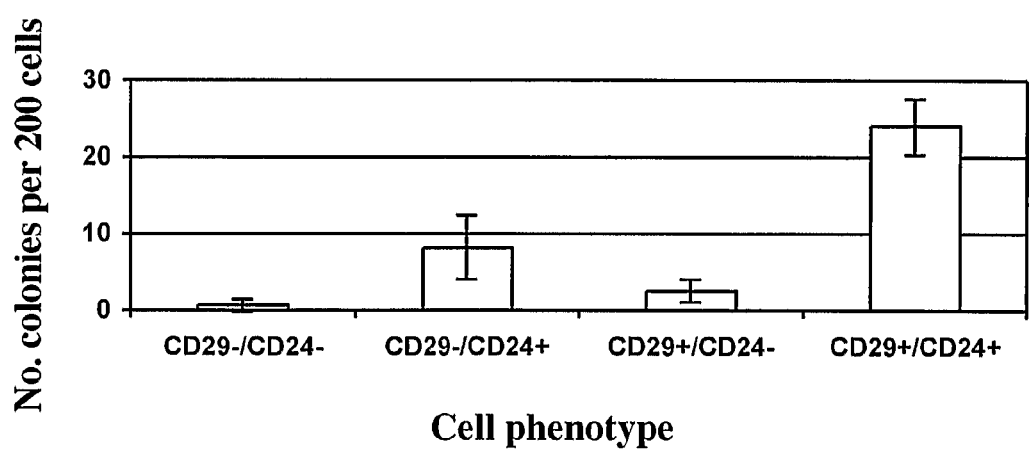

The ability of CD45$^{lo}$Ter119$^{lo}$CD31$^{lo}$ cells sorted by CD24 and CD29 staining to grow in short-term cultures was evaluated by plating 200 cells onto collagen coated plates and culturing the cells in DME-HAM containing BSA, 5 μg/ml insulin, 500 ng/ml hydrocortisone, 10 ng/ml EGF and 20 ng/ml cholera toxin at 37° C. and 5% CO$_2$/5% O$_2$ and determining the number of colonies at 5 days. Intriguingly, CD24$^+$CD29$^+$ cells reproducibly gave rise to the greatest number of colonies (FIG. 13), which were generally also larger. Thus colony formation appeared to correlate with the enhanced mammary gland repopulating capacity of these cells.

Example 10

Lin⁻CD29$^{hi}$CD24⁺ MaSCs

Cell surface markers are identified which are expressed on MaSCs and their derivatives in freshly isolated mammary cell suspensions. Since the mammary gland comprises a heterogeneous mix of cell types, including epithelium, endothelium, stromal and haemopoietic cells, antibodies were conveniently employed against endothelial (CD31) and haemopoietic (CD45 and TER119) antigens to deplete these cells. The substantial CD45⁺ and CD31⁺ populations were excluded by gating on the CD45⁻CD31⁻TER119⁻(Lin⁻) population. A limiting dilution analysis (Fazekas de St, *J Immunol Methods* 49:R11-23, 1982), analogous to that employed for the haemopoietic stem cell, to determine the frequency of mammary repopulating 'units' (MRUs) in defined subpopulations of cells. Lin⁻ cells were isolated by fluorescence-activated cell sorting (FACS) and transplanted in decreasing numbers into the mammary fat pads (MFPs) of recipient mice. The percentage of characteristic outgrowths containing all requisite epithelial elements (see Methods) was established for each injected cell number, and the frequency of MRUs in the Lin⁻ population calculated to be 1/4,900 (Table 2). An example of an outgrowth arising from 5,000 transplanted Lin⁻ cells is shown in FIG. 1b. In contrast, twenty-two transplants of 3,000 cells from the Lin⁺ gate produced no outgrowths in three independent experiments, indicating that MRUs are not enriched in this subset (FIG. 13b).

Four distinct Lin⁻ subpopulations were defined based on the expression of CD24 (heat stable antigen), which has been used to enrich neural stem cells and is expressed on human breast tumors, and CD29 (1-integrin), a stem cell marker in skin that has also been implicated in stem cell regulation in two expression profiling studies (FIG. 13c). The frequency of MRUs in these four populations was determined following isolation by FACS and mammary fat pad transplantation in numbers proportional to their frequency in the Lin⁻ population. The MRUs were enriched approximately eight-fold in the Lin⁻CD29$^{hi}$CD24⁺ population, whereas no significant enrichment was found in the other three subsets (Table 3). Co-staining for CD49f (α6 integrin) expression revealed significant enrichment of CD49f⁺⁺ cells in the Lin⁻CD29$^{hi}$CD24⁺ gate. Interestingly, the Lin⁻CD29$^{hi}$CD24⁺ population increased with age, but not with parity. These cells, therefore, appearED to be distinct from a larger mammary epithelial cell population induced by pregnancy and recently described to have stem cell-like characteristics.

The purification method was refined by double-sorting, counting and determining the viability of cells prior to transplantation. Moreover, transplanted cells from Rosa 26 mice, which carry a ubiquitously expressed LacZ transgene (Friedrich and Sorinao, *Genes Dev* 5:1513-1523, 1991), into wild-type recipients to allow verification of donor origin by staining for LacZ (β-galactosidase) activity in the harvested gland. Using this more quantitative method, the calculated MKU frequency in the Lin⁻CD29$^{hi}$CD24⁺ population was increased to 1/64 without being significantly altered for the other populations (Table 4). FIG. 13d depicts a LacZ-positive (LacZ⁺) epithelial outgrowth obtained from one of these transplants. Given that cells are inevitably lost during transplantation, the actual MRU frequency in the Lin⁻CD29$^{hi}$CD24⁺ population is likely to be higher than 1/64.

The expression of Sca-1\Ly6A\E was assessed in the Lin⁻CD29$^{hi}$CD24⁺ subpopulation. However, co-staining for Sca-1, CD29 and CD24 revealed no significant Sca-1$^{hi}$ population within the Lin⁻CD29$^{hi}$CD24⁺ gate (FIG. 13e, left panel). To confirm this observation in vivo, cells fractionated on the basis of Sca-1 expression and size were transplanted (FIG. 13e, right panel). The MRU frequency was at least three-fold higher in the smaller-sized, Sca-1$^{lo}$ population than the Sca-1$^{hi}$ or large-sized populations (Table 5). It was found that Sca-1 expression was substantially elevated on mammary epithelial cells cultured for 3 days.

Several types of stem cells, but not all, have an increased ability to exclude dyes such as Hoechst$_{33342}$, due to expression of membrane transporter proteins. Those that have this ability include haemopoietic, neural and myogenic, while spermatogonial stem cells do not. In the mammary gland, cells in the Hoechst side population (SP), which exhibit increased dye efflux, have been reported to be enriched for progenitor activity. However, the Hoechst SP were found to be depleted in the Lin⁻CD29$^{hi}$CD24⁺ gate by co-staining with Hoechst, CD29 and CD24. It was possible, therefore, to determine the MRU frequency in the side- and main-populations (MP) in vivo (FIG. 1f). While MP cells reliably gave rise to epithelial outgrowths, those from the SP did not. The calculated MRU frequency of MP cells was 1/2,900, similar to that of the Lin⁻ population. Exclusion of SP cells from the Lin⁻ population did not reduce the frequency of MRUs within it. It is concluded that there is no enrichment of MaSCs in the SP fraction, although some mammary progenitors may reside within it.

Figure 14:
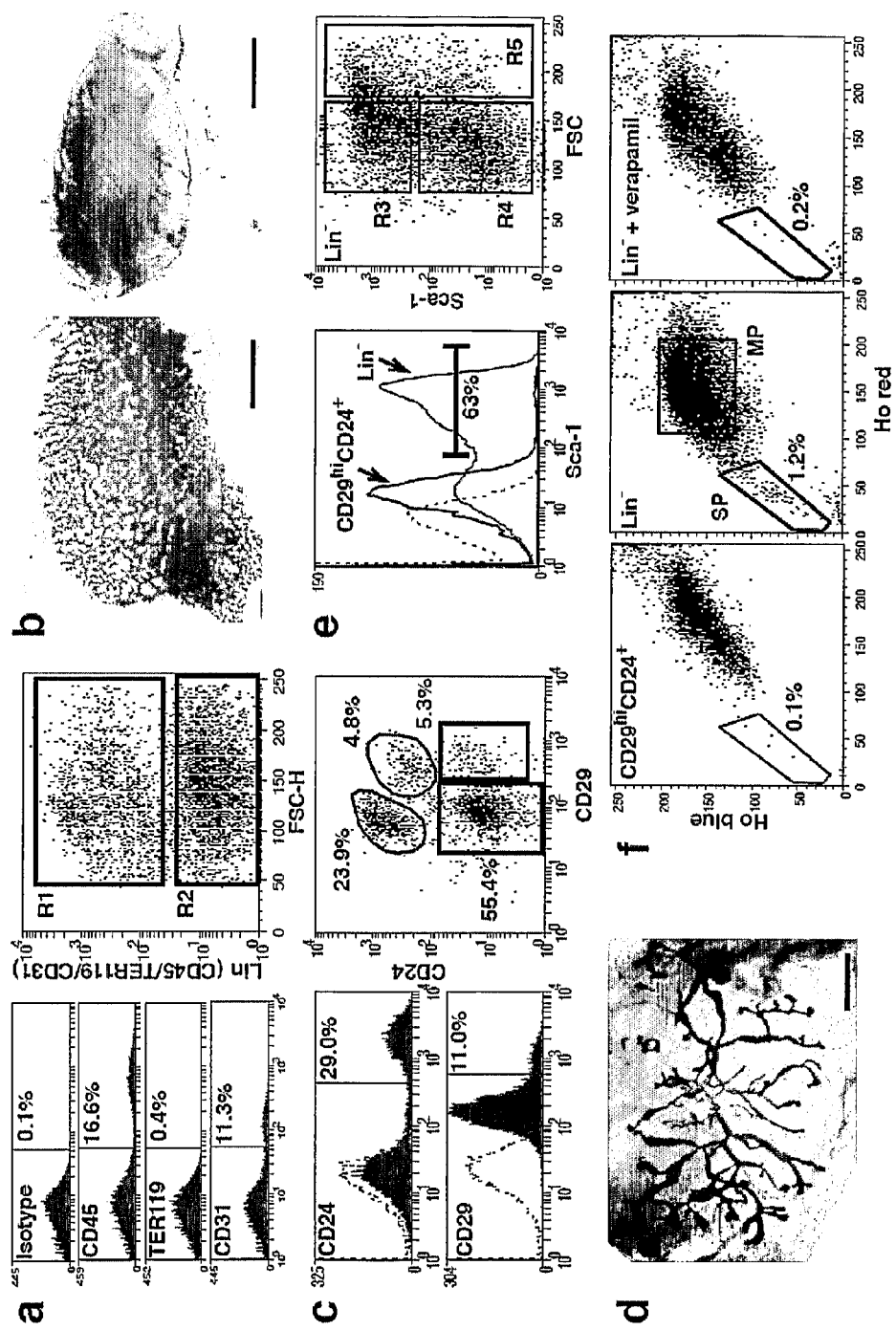
FIG. 14 are representations showing enrichment of MRUs in the Lin$^-$CD29$^{hi}$CD24$^+$ population. a, Expression of haemopoietic (CD45, Lin(TER119) and endothelial (CD31) lineage cell surface markers in mammary cell suspensions (left panel); gating strategy used to select Lin$^-$ (right panel, R2 gate) and Lin$^+$ (right panel, R1 gate) cells for limiting dilution transplant analysis. b, Typical haematoxylin-stained wholemounts of MFPs transplanted with 5,000 Lin$^-$ (left panel) and 3,000 Lin$^+$ cells (right panel). Bar: 750 µm. c, Expression of CD24 and CD29 in the Lin$^-$ population (left panel); gating strategy used to purify cells from the four Lin$^-$ populations defined by CD29 and CD24 expression for transplantation (right panel, percentages shown are typical values). d, A LacZ$^+$ outgrowth arising from the transplantation of 13 visualized, double-sorted Lin$^-$CD29$^{hi}$CD24$^+$ cells. Bar: 250 µm. e, Expression of Sca-1 in the Lin$^-$CD29$^{hi}$CD24$^+$ population (left panel, dotted line shows isotype labelling); gating strategy used to purify cells according to Sca-1 expression and size for transplantation (right panel, gates R3-5). f, Depletion of Hoechst SP cells in the Lin$^-$CD29$^{hi}$CD24$^+$ subpopulation (left panel) compared to the overall Lin$^-$ population (central panel); gating strategy used to purify cells according to Hoechst staining (central panel); loss of SP cells in the Lin$^-$ population induced by addition of 100 mM verapamil (right panel).

Further evidence that the Lin⁻CD29$^{hi}$CD24⁺ population is enriched for mammary progenitor cells came from cell culture assays for epithelial cell colonies. Only the two CD24⁺ populations yielded significant colonies and the Lin⁻CD29$^{hi}$CD24⁺ subset exhibited a 2- to 3-fold higher frequency, with substantially larger colonies (FIG. 14a). To assess the differentiation capacity of the cells, the growth of Lin⁻CD29$^{hi}$CD24⁺ and Lin⁻CD29$^{lo}$CD24⁺ cells in Matrigel were compared under lactogenic conditions. Cells from the Lin⁻CD29$^{lo}$CD24⁺ population only formed single-cell layered, alveolar-like structures that produced milk protein upon prolactin stimulation (FIG. 14b, top row). This population may therefore contain progenitor cells with a limited differentiative capacity. In contrast, Lin⁻CD29$^{hi}$CD24⁺ cells formed a heterogeneous mix of morphologically distinguishable structures, including ductal forms and multicellular spheroid bodies, as well as occasional alveolar-like, milk-producing structures akin to those from the Lin⁻CD29$^{lo}$CD24⁺ population (FIG. 14b, bottom row). The expanded differentiative repertoire of Lin⁻CD29$^{hi}$CD24⁺ cells, as well as their enhanced colony-forming ability, indicates that this population is enriched for mammary progenitors. Compatible with these findings, high levels of diffuse CD29 expression were apparent in the cap cell region of terminal end buds, presumed to be rich in stem cells, relative to mature ducts in which high expression was predominantly restricted to the baso-lateral regions, (FIG. 14c).

In order to test the 'common-progenitor model' of lineage development in the mammary gland, it was determined whether the Lin⁻CD29$^{hi}$CD24⁺ MRU constituted a single cell. Lin⁻CD29$^{hi}$CD24⁺ cells from Rosa 26 mice were counted after double-sorting, and resuspended at a concentration of one cell per injection volume, with or without supporting cells (5×10³) from a wild-type population depleted of Lin⁻CD29$^{hi}$CD24⁺ cells. Eight LacZ⁺ epithelial outgrowths were produced from 68 injections (Table 3). Notably, supporting cells did not affect the likelihood of an outgrowth or its size. Although the eight outgrowths could have resulted from more than one lineage-restricted progenitor, calculations showed this to be extremely unlikely. In relation to the statistical analysis, mammary repopulating cell frequencies were calculated using the R statistical software (R Development Core Team, 2004, http://www.R-project.org) generalized linear model function and L-Calc limiting dilution analysis software (Stem Cell Technologies, Vancouver, Canada), based on the proportion of negative results and Poisson statistics. The probability of the number of mammary repopulating cells in an aliquot from a cell suspension was calculated using a simulation program and the R statistical software, assuming the presence of cell aggregates in a Poisson distribution at proportions observed empirically in parallel experiments (26% doublets, 1% triplets).

In the 'single cell suspension' transplant assays the probability that 8/68 injections contained two or more different cells required for the development of all mammary epithelial lineages was calculated to be 0.01, based on the above assumptions, and conservatively estimating a ⅓ frequency of MRUs in the Lin$^-$CD29$^{hi}$CD24$^+$ population. The outgrowths from these assays are thus extremely likely to have arisen from a single cell.

In the self-renewal assays, the probability that each primary outgrowth of 25 or less cells arose from more than one cell was calculated to be 0.05, based on the calculated MRC frequency of 1/64 and assuming a Poisson distribution of cell number per aliquot. As the minimum number of secondary outgrowths was four, the chance that at least four MRCs were present in the primary transplants was calculated to be <0.007. The primary outgrowths were thus very likely to be clonal, and it is extremely likely that self-renewal occurred in primarily transplanted MaSCs.

Figure 15:
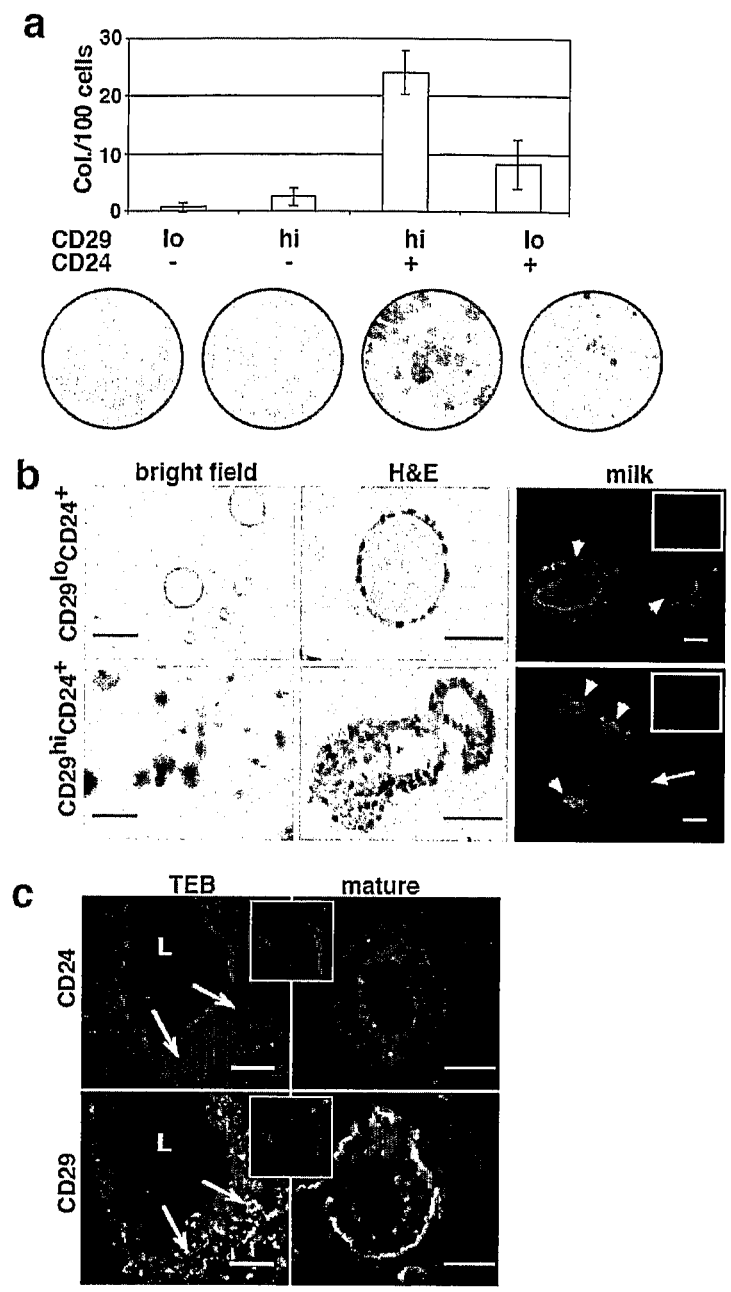
FIG. 15 are representations showing in vitro evidence for the increased progenitor capacity of Lin$^-$CD29$^{hi}$CD24$^+$ mammary cells. a, Colony-forming ability of the four Lin$^-$ cell populations defined by CD29 and CD24 expression (histogram shows mean±SEM, n=5). b, Representative structures produced by Matrigel culture of Lin$^-$CD29$^{lo}$CD24$^+$ and Lin$^-$CD29$^{hi}$CD24$^+$ cells (upper and lower panels respectively); bright field views of gels (left panels; Bar: 100 µm), H&E-stained sections (central panels; Bar: 10 µm), and labelling with anti-milk antibody are shown (right panels, arrowheads indicate milk-producing structures; arrow indicates a non-milk-producing structure; insets show isotype-labelled control sections: red, milk; blue, DAPI; Bars: top 40 µm, bottom 20 µm). c, Expression of CD24 and CD29 in a terminal end bud (left panels, arrows indicate cap cell region; Bar: 40 µm) and a more mature ductal structure (right panel; Bar: 16 µm). Insets show isotype-labelled control sections: red, CD24; green, CD29; blue, DAPI.

To prove definitively that a single cell can completely repopulate a cleared fat pad, individual, double-sorted Lin$^-$CD29$^{hi}$CD24$^+$ Rosa cells that had been viewed microscopically in 10 µl Terasaki wells were transplanted. Four LacZ$^+$ outgrowths were produced from 70 transplants involving two separate experiments (Table 6 and FIG. 15a) and, as previously observed, the presence of supporting cells had no effect. Substantial engraftment of the fat pad was evident and histological sectioning of the outgrowths revealed normal ductal structures composed of both myoepithelial and luminal epithelial cells (FIG. 15b). Furthermore, immunofluorescence staining of mammary gland sections derived from a pregnant recipient revealed milk protein within ductal lumens (FIG. 15c). Thus, a single Lin$^-$CD29$^{hi}$CD24$^+$ cell can reconstitute an entire mammary gland, demonstrating its high proliferative and multipotent differentiative capacity.

To evaluate whether the Lin$^-$CD29$^{hi}$CD24$^+$ mammary repopulating cell can self-renew, epithelial outgrowths derived from primary transplants of Lin$^-$CD29$^{hi}$CD24$^+$ cells were analysed by flow cytometry and re-transplanted. The primary transplant outgrowths comprised the same CD29 and CD24 profiles as wild-type mice (FIG. 15d), whereas cell suspensions from untransplanted mammary fat pads were CD24$^-$ (FIG. 15d), demonstrating that the CD24$^+$ cells were donor-derived. For secondary transplantation, primary transplants were used that developed from fewer than 26 double-sorted Lin$^-$CD29$^{hi}$CD24$^+$ Rosa cells and that therefore were very likely derived from a single cell. Cells from each of the primary outgrowths, verified by PCR analysis for the LacZ gene, generated LacZ$^+$ outgrowths in at least four recipients (FIG. 15e and Table 3). Thus the Lin$^-$CD29$^{hi}$CD24$^+$ mammary repopulating cell is capable of self-renewal, a defining feature of stem cells (Weissman, Cell 100:157-168, 2000).

Figure 16:
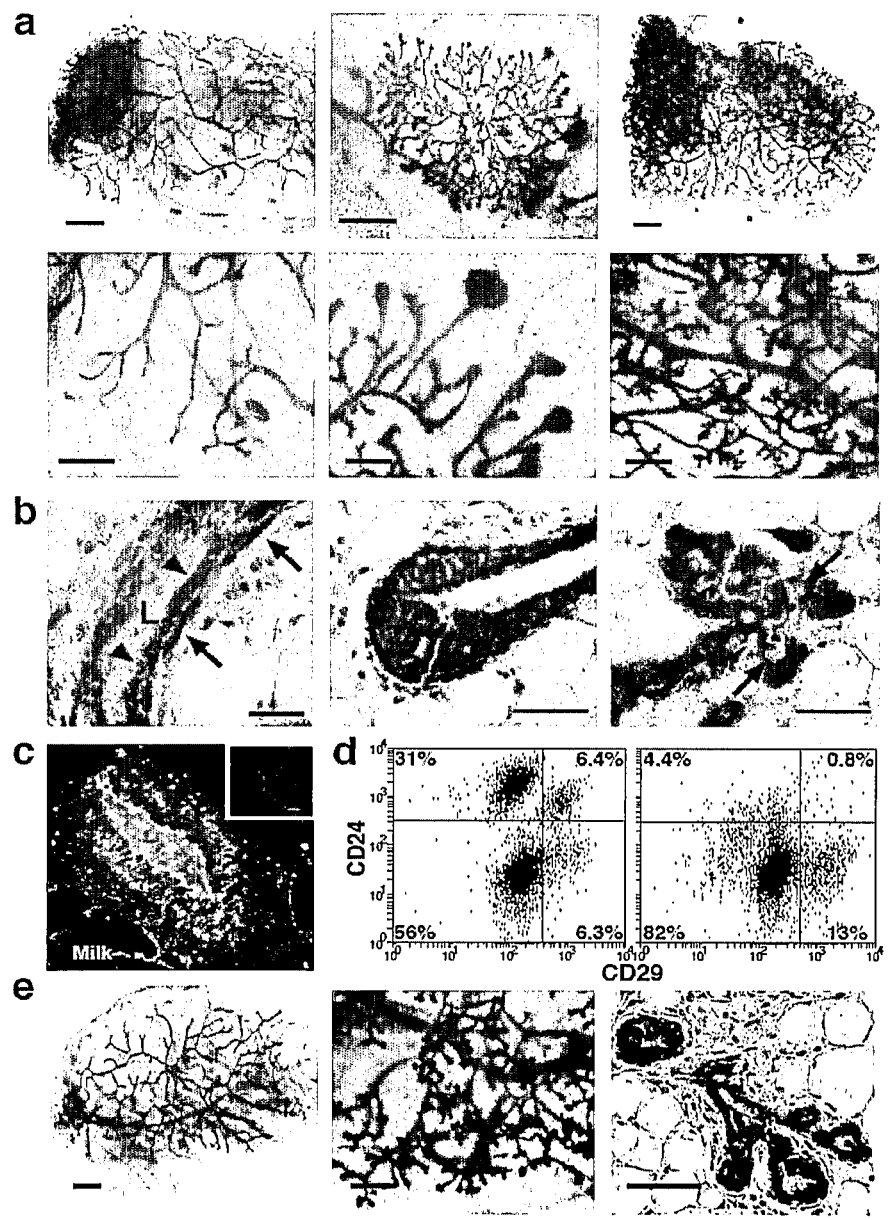
FIG. 16 are representations showing a single, self-renewing Lin$^-$CD29$^{hi}$CD24$^+$ cell can repopulate a MFP. a, Wholemount analysis of epithelial outgrowths arising from the transplantation of a single LacZ$^+$ Lin$^-$CD29$^{hi}$CD24$^+$ cell; low magnification image of outgrowths shown for virgin recipient MFPs harvested 10 and 8.5 weeks after transplantation (upper left and upper central panels, respectively; Bar: 250 µm), and a pregnant recipient harvested 10 weeks after transplantation (upper right panel; Bar: 250 µm); high magnification image of virgin ductal-lobular structures (lower left panel; Bar: 100 µm), TEBs (lower central panel; Bar: 50 µm), and developing lobulo-alveolar structures in a pregnant recipient (lower right panel; Bar: 100 µm). b, Sections of single-cell origin, LacZ$^+$ outgrowths stained with nuclear fast red show ductal luminal (left panel, arrowheads; Bar: 5 µm) and myoepithelial (left panel, arrows) cell lineages and a characteristic terminal end bud (central panel; Bar: 10 µm) in a virgin recipient, and lobulo-alveolar epithelium in a pregnant recipient (right panel, arrows indicate lipid droplets associated with milk production; Bar: 10 µm). c, Immunofluorescence staining with anti-milk antibody of a duct arising from a single LacZ$^+$ Lin$^-$CD29$^{hi}$CD24$^+$ cell in a recipient at mid-pregnancy; inset shows isotype-labelled control section: green, milk; blue, DAPI. d, Flow cytometric analysis of cell suspensions prepared from MFPs transplanted with Lin$^-$CD29$^{hi}$CD24$^+$ cells (left panel) and untransplanted cleared MFPs (control, right panel). e, Low and high power magnification views of virgin and pregnant recipient MFPs (left and central panels; Bars: 250 and 100 µm, respectively), containing LacZ$^+$ outgrowths that arose from secondary transplantation of cells from a primary outgrowth of 25 Lin$^-$ CD29$^{hi}$CD24$^+$ cells; section of a secondary LacZ$^+$ outgrowth in a pregnant recipient stained with nuclear fast red (right panel; Bar: 20 μm).
Figure 17:
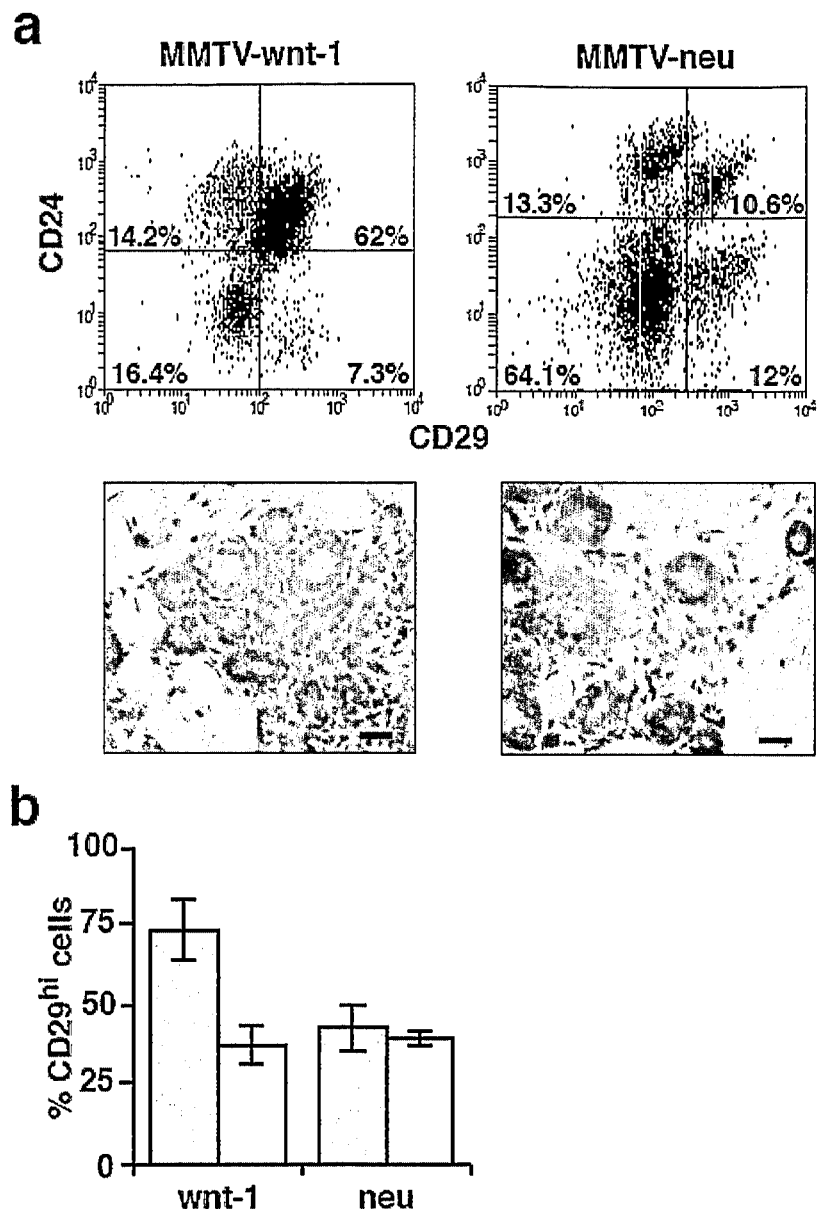
FIG. 17 are representations showing that the Lin$^-$CD29$^{hi}$CD24$^+$ population is expanded in MMTV-Wnt-1 transgenic mice. a, Representative flow cytometric analyses of CD24 and CD29 expression in cell suspensions from MMTV-Wnt-1 and MMTV-neu transgenic mammary glands. Macroscopically normal mammary tissue was taken from multiparous MMTV-Wnt-1 mice at 4 months and virgin MMTV-neu mice at 6 months of age (n=3). Lower panel: H&E stained sections from the same premalignant, hyperplastic glands. Bars: 40 μm. b, Histogram depicting the percentages of CD29$^{hi}$ cells in the Lin$^-$CD24$^+$ (epithelial) populations of MMTV-Wnt-1 (left-shaded histogram, n=3; 74%) and MMTV-neu (right-shaded histogram, n=3; 43%) transgenic mammary glands compared with age- and parity-matched controls (unshaded histograms, n=2; 38% and 40%, respectively,). Percentages shown are means±SEM.

Evidence supports the existence of a tumor stem cell for breast cancer (Al-Hajj et al, 2004, Supra). The expression of the stem cell markers CD29 and CD24 in two strains of mice prone to develop mammary tumors was, therefore, examined. Hyperplastic but premalignant mammary tissue harvested from multiparous female MMTV-Wnt-1 mice showed a marked expansion of the Lin$^-$CD29$^{hi}$CD24$^+$ subpopulation (FIG. 16a) and the percentage of CD29$^{hi}$ cells within the epithelial CD24$^+$ population was two-fold higher in transgenic mice than control mice (FIG. 16b). The findings are compatible with the proposal that the MMTV-Wnt-1 oncogene gives rise to heterogeneous tumors because it targets undifferentiated progenitors or stem cells. Further, the Wnt signalling pathway may regulate self-renewal of MaSCs, in parallel with its role in haemopoietic stem cells. In contrast, pre-neoplastic mammary tissue from MMTV-neu mice, which succumb to luminal epithelial tumors, showed no expansion of the stem cell-enriched population (FIGS. 16a, b). The data support the hypotheses that mammary tumors in the MMTV-Wnt-1 mice arise from a stem cell population and that a distinct epithelial cell type is the target of transformation in the MMTV-neu tumorigenesis model.

This study provides the first description of reconstitution of an entire organ from a single epithelial stem cell and should have implications for the isolation of stem cells from other epithelial tissues. Within the mammary gland, delineation of the genes that govern stem cell function and lineage commitment should ultimately allow the identification of novel markers of normal progenitor and breast cancer stem cells.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 2

FREQUENCY OF MRUS IN LIN$^-$ MAMMARY CELLS

| Number of cells per MFP | Number of outgrowths* | MRU frequency (upper and lower limit) |
| --- | --- | --- |
| 1,250 | 0/4 | 1/4,900 |
| 2,500 | 3/9 | (1/3,200-1/7,500) |
| 5,000 | 7/13 | |
| 10,000 | 10/10 | |
| 20,000 | 10/10 | |
| >20,000 | 14/14 | |

Wild-type cells from the Lin$^-$ gate were injected at the indicated number (based on machine counts) into the cleared MFPs of three-week-old recipients, and the MFPs analysed as described in Table 1. Data are from seven independent experiments.
*Shown as number of outgrowths per number of injected MFPs.

TABLE 3

FREQUENCY OF MRUS IN SUBSETS OF LIN$^-$ MAMMARY CELLS DEFINED BY CD29 AND CD24 EXPRESSION

| Phenotype | Number of cells per MFP | Number of outgrowths* | MRU frequency (upper and lower limit) |
| --- | --- | --- | --- |
| CD29$^{lo}$ CD24$^-$ | 2,300 | 0/6 | 1/147,000 |
| | 2,400 | 0/8 | (1/37,000-1/590,000) |
| | 8,500 | 0/8 | |
| | 9,200 | 1/4 | |
| | 9,300 | 1/10 | |
| | 12,000 | 0/6 | |
| CD29$^{lo}$ CD24$^+$ | 190 | 0/6 | <1/21,000† |
| | 220 | 0/8 | (1/3,000-1/150,000) |
| | 400 | 0/7 | |
| | 430 | 0/8 | |
| | 600 | 0/10 | |

TABLE 3-continued

FREQUENCY OF MRUS IN SUBSETS OF LIN⁻ MAMMARY CELLS
DEFINED BY CD29 AND CD24 EXPRESSION

| Phenotype | Number of cells per MFP | Number of outgrowths* | MRU frequency (upper and lower limit) |
|---|---|---|---|
| | 650 | 0/10 | |
| $CD29^{hi} CD24^+$ | 18 | 0/5 | 1/590 |
| | 20 | 0/9 | (1/300-1/1,100) |
| | 60 | 2/7 | |
| | 100 | 3/11 | |
| | 200 | 3/10 | |
| | 200 | 1/11 | |
| $CD29^{hi} CD24^-$ | 54 | 0/9 | 1/2,900 |
| | 120 | 1/6 | (1/1,100-1/7,800) |
| | 170 | 0/7 | |
| | 260 | 0/6 | |
| | 420 | 1/8 | |
| | 580 | 2/9 | |

Wild-type cells from the four Lin⁻ subsets defined by CD24 and CD29 expression were injected at the indicated number (based on machine-counts) into the cleared MFPs of three-week-old recipients, and the MFPs analysed as described in Table 1. Data are from six independent experiments.
*Shown as number of outgrowths per number of injected MFPs.
†Calculated assuming one mouse transplanted with the maximum number of cells had developed an outgrowth.

TABLE 4

FREQUENCY OF MRUS IN DIFFERENT SUBSETS OF DOUBLE-
SORTED, VISUALISED LIN⁻ MAMMARY CELLS
BASED ON EXPRESSION OF CD29 AND CD24

| Phenotype | Number of cells per MFP | Number of outgrowths* | MRU frequency (upper and lower limit) |
|---|---|---|---|
| $CD29^{lo} CD24^+$ | 100-109 | 0/6 | <1/3,300† |
| | 110-119 | 0/9 | (1/470-1/24,000) |
| | 120-129 | 0/6 | |
| | 130-139 | 0/7 | |
| | 140-149 | 0/2 | |
| $CD29^{hi} CD24^-$ | 90-99 | 0/2 | <1/3,300† |
| | 100-109 | 0/7 | (1/460-1/23,000) |
| | 110-119 | 0/9 | |
| | 120-129 | 0/7 | |
| | 130-139 | 0/4 | |
| $CD29^{hi} CD24^+$ | 10-19 | 3/38 | 1/64 |
| | 30-49 | 6/6 | (1/53-1/74) |
| | 50-79 | 13/17 | |
| | 80-99 | 6/8 | |
| | 100-149 | 9/12 | |

LacZ⁺ cells from the Lin⁻CD29$^{lo}$CD24⁺, Lin⁻CD29$^{hi}$CD24⁻ and Lin⁻CD29$^{hi}$CD24⁺ populations were double sorted, counted and injected at the indicated number into the cleared MFPs of three-week-old recipients. Five to eight weeks later the recipients were killed as virgins, and their MFPs examined for the presence of epithelial outgrowths. The MRU frequency for each cell population was calculated with L-cal software, using the median of the stated range as the number of cells transplanted.
*Shown as number of outgrowths per number of injected MFPs.
†Calculated assuming one mouse transplanted with the maximum number of cells had developed an outgrowth.

TABLE 5

HOECHST$_{33342}$ EXCLUSION AND HIGH SCA-1 EXPRESSION
DO NOT DEFINE MRU ENRICHED SUBSETS IN
LIN⁻ MAMMARY CELLS.

| Phenotype | Number of cells per MFP | Number of outgrowths* | MRU frequency (upper and lower limit) |
|---|---|---|---|
| Small Sca-1$^{hi}$ (R3) | 2,100 | 0/6 | 1/30,000 |
| | 2,300 | 0/5 | (1/10,000-1/93,000) |
| | 3,300 | 2/13 | |
| | 3,600 | 1/8 | |
| Small Sca-1$^{mid-lo}$ (R4) | 1,900 | 2/7 | 1/8,900 |
| | 2,400 | 2/5 | (1/5,100-1/16,000) |
| Large Sca-1$^{lo-hi}$ (R5) | 4,800 | 7/16 | 1/37,000 |
| | 5,200 | 2/8 | (1/5,200-1/260,000) |
| | 1,100 | 0/7 | |
| | 1,300 | 1/9 | |
| | 2,000 | 0/4 | |
| | 2,100 | 0/6 | |
| HOECHST-MP | 2,400 | 3/6 | 1/2,900 |
| | 2,800 | 1/3 | (1/1,600-1/5,100) |
| | 3,700 | 3/4 | |
| | 5,700 | 4/4 | |
| | 11,000 | 4/4 | |
| | 15,000 | 4/4 | |
| HOECHST-SP | 37 | 0/6 | 1/3,300 |
| | 65 | 0/3 | (1/470-1/23,000) |
| | 75 | 0/4 | |
| | 130 | 0/4 | |
| | 260 | 0/4 | |
| | 300 | 1/4 | |

Wild-type cells from the R3, R4, R5 (FIG. 1e), MP or SP (FIG. 1f) sorting windows were injected at the indicated number into the cleared MFPs of three-week-old recipients, and the MFPs analysed as described in Table 1. Data are from three independent experiments for each marker.
*Shown as number of outgrowths per number of injected MFPs.

TABLE 6

OUTGROWTHS FROM SINGLE LIN⁻CD29$^{HI}$CD24⁺ CELLS

| | Number of cells per primary transplant | Supporting cells | Number of outgrowths* |
|---|---|---|---|
| Primary transplants† | | | |
| Single cell suspension | 1 | – | 3/33 |
| | 1 | + | 5/35 |
| Visualized single cells | 1 | – | 2/32 |
| | 1 | + | 2/38 |
| Secondary transplants§ | | | |
| | 25 | – | 17/18 |
| | 14 | – | 11/18 |
| | 22 | – | 4/18 |
| | 23 | – | 12/12 |
| | 24 | – | 7/16 |

Single LacZ⁺ cells sorted from Rosa 26 mice were injected into the cleared MFPs of three-week-old recipients, and the MFPs analysed as described in Table 4.
†Cells were taken either from a single cell suspension containing 1 cell per 10 μl, or from individual 10 μl aliquots in which a single cell had been visualized. Data from each of these single cell transplant approach are pooled from two independent experiments.
*Shown as number of LacZ⁺ outgrowths per number of injected MFPs.
§Cells from LacZ⁺ outgrowths derived from the indicated primary transplant cell number were secondarily transplanted into cleared MFPs. Data from five independent experiments are shown.

BIBLIOGRAPHY

Al-Hajj et al., *PNAS* 100:3983-3988, 2004.
Akimaru et al., *Cytokines Mol Ther* 1: 197-210, 1995.
Alley et al., *Cancer Res* 48: 589-601, 1988.
Alvi et al., *Breast Cancer Res* 5:R1-R8, 2003.
Alving et al., *Immunol Rev* 145:5-31, 1995.
Atherton and Shephard, *Synthetic Vaccines*, Blackwell Scientific Publications.
Ausubel et al., *Current Protocols in Molecular Biology*, John Wiley & Sons Inc, 1994-1998.
Cavanaugh et al., *Investigational New Drugs* 8:347-354. 1990.
Cook et al., *Anal Biochem* 179:1-7, 1989.

Crowley et al. *J Immunol Methods* 133: 55-66, 1990.
Daniel et al., *PNAS* 61:53-60, 1968.
DeOme et al., *Cancer Res* 19:515-520, 1959.
Egleton and Davis, *Peptides* 18:1431-1439, 1997.
Fazekas de St, *J Immunol Methods* 49:R11-23, 1982.
Fix, *Pharm Res* 13:1760-1764, 1996.
Francis, *Differentiation* 57:63-75, 1994.
Friedrich and Sorinao, *Genes Dev* 5:1513-1523, 1991.
Goodall et al., *J Exp Med* 183:1797-1806, 1996.
Langer, *Science* 249:1527-1533, 1990.
Li et al., *Nat Med* 9:1293-1299, 2003.
Marshall et al., *Growth Reg* 5: 69-84, 1985.
Morris et al., *Nat Biotech* 22:411-417, 2004.
Mosmann, *J Immunol Methods* 65: 55-63, 1983.
Patton, *Nat Biotech* 16:141-143, 1998.
Porstmann et al., *J Immunol Methods* 82:169-179, 1985.
Putney and Burke, *Nat Biotech* 16:153-157, 1998.
Raes, *Adv Anim Cell Biol Technol Bioprocesses*, Butterworths, London, pp 161-171, 1989.
Remington's Pharmaceutical Sciences, 18$^{th}$ Edition, Mack Publishing Company, Easton, Pa., 1990.
Reya et al., *Nature* 414:105-111, 2001.
Rietze et al., *Nature* 214:736-739, 2001.
Roberge et al., *Science* 269: 202, 1995.
Samanen et al., *J Pharm Pharmacol* 48:119-135, 1996.
Sambrook, et al., *A Molecular Cloning—A Laboratory Manual*, Cold Spring Harbour, New York, USA, 1989.
Sayani and Chien, *Crit Rev Ther Drug Carrier Syst* 13:85-184, 1996.
Scudiero et al., *Cancer Res* 48: 4827-4833, 1988.
Smalley and Ashworth, *Nat Rev Cancer* 3:832-844, 2003.
Suntres and Shek, *J Pharm Pharmacol* 46:23-28, 1994.
Szoka and Papahadjopoulos, *Ann Rev Biophys Bioeng* 9:467-508, 1980.
Tumbar et al., *Science* 303:359-363, 2004.
Vutla et al., *J Pharm Sci* 85:5-8, 1996.
Watt, *FASEB* 5:281-284, 1991.
Weissman, *Cell* 100:157-168, 2000
Welm et al., *Dev Biol* 245:42-56, 2002.
Woodle et al., *Pharm Res* 9:260-265, 1992.
Zalipsky et al., *Bioconjug Chem* 6:705-708, 1995.

The invention claimed is:

1. A method for isolating a substantially homogeneous population of mammary stem (MaSCs) cells comprising:
   obtaining mammary tissue;
   disrupting said mammary tissue to provide a heterogenous population of cells comprising the MaSCs to be isolated;
   contacting the heterogeneous population of cells with specific binding partners for each of the following markers: CD45, TER119, CD31, CD24 and CD29; and
   selecting cells in the heterogeneous population that demonstrate a low amount of binding to the specific binding partners for CD45, TER119, CD31 and a high amount of binding to the specific binding partners for the CD24 and CD29 markers such that said cells are CD45$^{lo}$TER119$^{lo}$CD31$^{lo}$CD24$^{hi}$CD29$^{hi}$,
   thereby obtaining a substantially homogeneous population of MaSCs.

2. The method of claim 1 wherein the cells are from a human.

3. The method of claim 1 wherein the cells are from a mouse.

4. The method of claim 1 wherein the selecting is by fluorescence activated cell sorting (FACS).

5. A substantially homogenous population of MaSCs selected according to a method comprising:
   obtaining mammary tissue;
   disrupting said mammary tissue to provide a heterogenous population of cells comprising the MaSCs to be isolated;
   contacting the heterogeneous population of cells with specific binding partners for each of the following markers: CD45, TER119, CD31, CD24 and CD29; and
   selecting cells in the heterogeneous population that demonstrate a low amount of binding to the specific binding partners for CD45, TER119, CD31 and a high amount of binding to the specific binding partners for the CD24 and CD29 markers, wherein said cells are CD45$^{lo}$TER119$^{lo}$CD31$^{lo}$CD24$^{hi}$CD29$^{hi}$, thereby obtaining the substantially homogeneous population of MaSCs,
   wherein said substantially homogenous population of MaSCs is at least 50% pure with regard to the CD45$^{lo}$TER119$^{lo}$CD31$^{lo}$CD24$^{hi}$CD29$^{hi}$ phenotype and is depleted of Hoechst$_{33342}$-effluxing side population (SP) cells compared to the number of SP cells in an overall CD45$^{lo}$TER119$^{lo}$CD31$^{lo}$ population isolated from said mammary tissue.

6. The homogenous population of claim 5 wherein the cells are from human.

7. The homogenous population of claim 5 wherein the cells are from mouse.

8. A method for cell replacement therapy in an organism, said method comprising:
   generating a substantially homogenous population of MaSCs according to the method of claim 1, and
   introducing said homogenous population of MaSCs to said organism or an organism which is capable of receiving said MaSCs.

9. A method for screening for a modulation of a substantially homogeneous population of MaSCs according to claim 5, said method comprising contacting said MaSCs with a putative modulator and screening for modulation of MaSC growth or development.

10. A substantially homogenous population of MaSCs, wherein at least 50% of the cells in the population are CD45$^{lo}$TER119$^{lo}$CD31$^{lo}$CD24$^{hi}$CD29$^{hi}$, and wherein said substantially homogenous population of MaSCs is depleted of Hoechst$_{33342}$-effluxing side population (SP) cells compared to the number of SP cells in an overall CD45$^{lo}$TER119$^{lo}$CD31$^{lo}$ population isolated from said mammary tissue.

11. A substantially homogenous population of MaSCs according to claim 5 that is at least 90% pure with regard to the CD45$^{lo}$TER119$^{lo}$CD31$^{lo}$CD24$^{hi}$CD29$^{hi}$ phenotype.

* * * * *